(12) United States Patent
Derwin et al.

(10) Patent No.: US 10,792,393 B2
(45) Date of Patent: Oct. 6, 2020

(54) REINFORCED TISSUE GRAFT

(71) Applicant: THE CLEVELAND CLINIC FOUNDATION, Cleveland, OH (US)

(72) Inventors: Kathleen A. Derwin, Shaker Heights, OH (US); Amit Aurora, Bedford, OH (US); Joseph P. Iannotti, Strongsville, OH (US); Jesse A. McCarron, Cleveland Heights, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 273 days.

(21) Appl. No.: 15/725,304

(22) Filed: Oct. 5, 2017

(65) Prior Publication Data

US 2018/0078678 A1    Mar. 22, 2018

Related U.S. Application Data

(62) Division of application No. 12/934,791, filed as application No. PCT/US2009/038570 on Mar. 27, 2009, now abandoned.

(60) Provisional application No. 61/040,066, filed on Mar. 27, 2008.

(51) Int. Cl.
| | |
|---|---|
| *A61L 27/24* | (2006.01) |
| *A61F 2/02* | (2006.01) |
| *A61L 27/36* | (2006.01) |
| *A61F 2/08* | (2006.01) |
| *A61L 27/40* | (2006.01) |
| *A61L 27/54* | (2006.01) |
| *A61F 2/00* | (2006.01) |

(52) U.S. Cl.
CPC .......... *A61L 27/3633* (2013.01); *A61F 2/08* (2013.01); *A61L 27/40* (2013.01); *A61L 27/54* (2013.01); *A61F 2/0063* (2013.01); *A61L 27/3604* (2013.01)

(58) Field of Classification Search
CPC .. A61F 2/0063; A61F 2/02; A61F 2002/0068; A61L 27/3604; A61L 27/3633; A61L 27/3629; A61L 27/3641; A61L 27/38; A61L 27/3804; A61L 27/3839
See application file for complete search history.

(56) References Cited

U.S. PATENT DOCUMENTS

| | | | |
|---|---|---|---|
| 6,551,356 | B2 | 4/2003 | Rousseau |
| 6,638,312 | B2 | 10/2003 | Plouhar et al. |
| 6,736,854 | B2 | 5/2004 | Vadurro et al. |

(Continued)

FOREIGN PATENT DOCUMENTS

| | | |
|---|---|---|
| EP | 1177800 A1 | 6/2002 |
| KR | 20060059240 A | 6/2006 |

(Continued)

OTHER PUBLICATIONS

Cheng, Zhaokang, et al. "Trageted migration of mesenchymal stem cells modified with CXCR4 gene to infarcted myocardium improves cardiac performance." Molecular Therapy 16.3 (2008): 571-579.

(Continued)

*Primary Examiner* — Christopher L Templeton
(74) *Attorney, Agent, or Firm* — Tarolli, Sundheim, Covell & Tummino LLP

(57) ABSTRACT

A biocompatible tissue graft is provided. The tissue graft includes an extracellular matrix patch and a means for reinforcing the patch.

8 Claims, 15 Drawing Sheets

(56) References Cited

U.S. PATENT DOCUMENTS

| | | | |
|---|---|---|---|
| 6,800,082 B2 | 10/2004 | Rousseau | |
| 6,902,932 B2 | 6/2005 | Altman et al. | |
| 7,160,333 B2 | 1/2007 | Plouhar et al. | |
| 7,569,233 B2 | 8/2009 | Malaviya et al. | |
| 7,615,065 B2 | 11/2009 | Priewe et al. | |
| 2001/0002446 A1 | 5/2001 | Plouhar et al. | |
| 2002/0103542 A1 | 8/2002 | Bilbo | |
| 2003/0143207 A1 | 7/2003 | Livesey et al. | |
| 2003/0212460 A1* | 11/2003 | Darois | A61F 2/0063 623/23.64 |
| 2004/0006395 A1 | 1/2004 | Badylak | |
| 2004/0078090 A1 | 4/2004 | Binette et al. | |
| 2005/0249771 A1 | 11/2005 | Malaviya et al. | |
| 2005/0249772 A1 | 11/2005 | Malaviya et al. | |
| 2006/0029639 A1 | 2/2006 | Morinaga et al. | |
| 2006/0253203 A1 | 11/2006 | Alvarado | |
| 2006/0282173 A1 | 12/2006 | McFetridge | |
| 2006/0286144 A1 | 12/2006 | Yang et al. | |
| 2007/0129811 A1 | 6/2007 | Plouhar et al. | |
| 2007/0162103 A1 | 7/2007 | Case et al. | |
| 2007/0190108 A1 | 8/2007 | Datta et al. | |
| 2007/0224238 A1 | 9/2007 | Mansmann et al. | |
| 2007/0260268 A1 | 11/2007 | Bartee et al. | |
| 2007/0276507 A1 | 11/2007 | Bertram et al. | |
| 2008/0027542 A1 | 1/2008 | McQuillan et al. | |
| 2008/0038352 A1 | 2/2008 | Simpson et al. | |
| 2008/0044900 A1 | 2/2008 | Mooney et al. | |
| 2008/0046009 A1* | 2/2008 | Albertorio | A61B 17/0401 606/232 |
| 2008/0178786 A1* | 7/2008 | Butcher | A61F 2/0063 112/439 |
| 2008/0188936 A1 | 8/2008 | Ball et al. | |
| 2008/0281421 A1 | 11/2008 | Cahn et al. | |
| 2009/0018655 A1 | 1/2009 | Brunelle et al. | |
| 2009/0306688 A1 | 12/2009 | Patel et al. | |
| 2009/0318752 A1 | 12/2009 | Evans et al. | |
| 2010/0020477 A1 | 1/2010 | Chen | |
| 2010/0028396 A1 | 2/2010 | Ward et al. | |
| 2010/0063599 A1 | 3/2010 | Brunelle | |
| 2010/0185219 A1 | 7/2010 | Gertzman et al. | |

FOREIGN PATENT DOCUMENTS

| | | |
|---|---|---|
| WO | 2003/007847 A1 | 1/2003 |
| WO | 2007/047743 A2 | 4/2007 |
| WO | 2009/120966 A2 | 10/2009 |
| WO | 2010/059783 A2 | 5/2010 |
| WO | 2012/047338 A2 | 4/2012 |

OTHER PUBLICATIONS

Post, Melvin. "Pectoralis major transfer for winging of the scapula." Journal of shoulder and elbow surgery 4.1 (1995): 1-9.
PCT International Search Report and Written Opinion, dated Mar. 6, 2014, pp. 1-11.
PCT International Search Report and Written Opinion, dated Mar. 6, 2014, pp. 1-12.
PCT International Search Report and Written Opinion, dated Mar. 13, 2014, pp. 1-8.
Aurora, Amit, et al. "Mechanical characterization and biocompatibility of a novel reinforced fascia patch for rotator cuff repair." Journal of Biomedical Materials Research Part A 99.2 (2011): 221-230.
Baker, Andrew R., et al. "Does augmentation with a reinforced fascia patch improve rotator cuff repair outcomes?." Clinical Orthopaedics and Related Research® 470.9 (2012): 2513-2521.
Bright, Robert W., and Wiliam T. Green. "Freeze-dried fascia lata allografts: a review of 47 cases." Journal of pediatric orthopedics 1.1 (1981): 13-22.
Haas, Franz, et al. "Reconstruction of combined defects of the Achilles tendon and the overlying soft tissue with a fascia lata graft and a free fasciocutaneous lateral arm flap." Annals of plastic surgery 51.4 (2003): 376-382.
Itani, Kamal MF, et al. "Prospective study of single-stage repair of contaminated hernias using a biologic porcine tissue matrix: the RICH Study." Surgery 152.3 (2012): 498-505.
McCarron, Jesse A., et al. "Reinforced fascia patch limits cyclic gapping of rotator cuff repairs in a human cadaveric model." Journal of shoulder and elbow surgery 21.12 (2012): 1680-1686.
Anon, "The stitching of fabrics, Part IV. The strength of seams", Shirley Institute Bulletin, 1939, pp. 164-175.
Designation D 1908-81, "Standard test method for needle-related damage due to sewing in woven fabric", ASTM International, pp. 384-388.
Aurora, Amit, et al. "Commercially available extracellular matrix materials for rotator cuff repairs: state of the art and future trends," Journal of shoulder and elbow surgery 16.5 (2007): S171-S178, APA.
Cheng, K. P. S., and K. P. W. Poon. "Studies on the seam properties of some selected soven fabrics." Conference Proceedings, Institute of Textiles and Clothing. 2002.
Choudhary, A. K., and Amit Goel. "Effect of some fabric and sewing conditions on apparel seam characteristics." Journal of Textiles 2013 (2013).
Danielson, Carl Christian, "Age-related thermal stability and susceptibility to proteolysis of rat bone collagen," Biochemical journal 272.3 (1990): 697-701.
Dransfield, Kimberley, Caroline Baillie, and Yiu-Wng Mai. "Improving the delamination resistance of CFRP by stitching—a review." Composites Science and Technology 50.3 (1994): 305-317.
Gribaa, Sabria, Sami Ben Amar, and Abdelwaheb Dogui. "Influence of sewing parameters upon the tensile behavior of textile assembly." International journal of clothing science and Technology 18.4 (2006): 235-246.
Gurarda, A., and B. Meric. "The effects of elastane yarn type and fabric density on sewing needle penetration forces and seam damage of PET/elastane woven fabrics." Fibres & Textiles in Eastern Europe 4 (63) (2007): 73-76.
Leikina, E., et al. "Type I collagen is thermally unstable at body temperature." Proceedings of the National Academy of Sciences 99.3 (2002): 1314-1318.
Mouritz, A. P., K. H. Leong, and I. Herszberg. "A review of the effect of stitching on the in-plane mechanical properties of fibre-reinforced polymer composites." Composites Part A: applied science and manufacturing 28.12 (1997): 979-991.
Murugesan, Bharani, et al. "Characterization of Sewability Parameters of Plain Structured Fabric with Structurally Modified Trevira CS Yarn for Defence Application." Chemical Science Review and Letters 1.2 (2012): 53-61. APA.
Sauri, R. Ma, et al. "A factorial study of seam resistance: woven and knitted fabrics." (1987).
Tong et al., "Chapter 8 stitched composites", 3D Fibre Reinforced Polymer Composites, Elsevier Science Ltd., 2002, pp. 162-204.
Shiyamaladevi et al., "Characterization of seam strength and seam slippage on cotton fabric with woven structures and finish", Res. J. Engineering Sci, vol. 1(2), pp. 41-50, Aug. 2012.
Singapore Search Report and Written Opinion for corresponding Application No. 11201503367V, dated Mar. 18, 2016, pp. 1-7.
Singapore Search Report and Written Opinion for corresponding Application No. 11201503364U, dated May 9, 2016, pp. 1-7.
Communication pursuant to Article 94(3) EPC, for corresponding Application No. 09 724 439.6, dated Oct. 2, 2015, pp. 1-4.

* cited by examiner

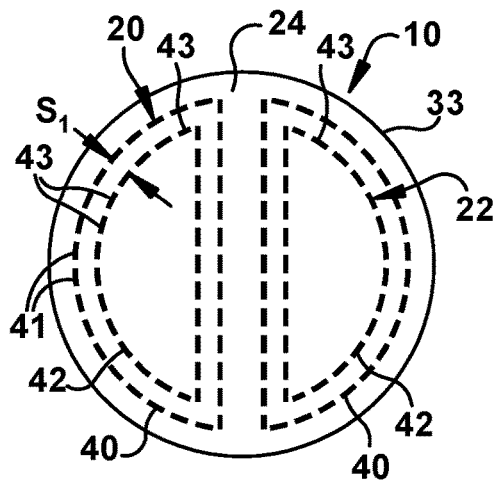
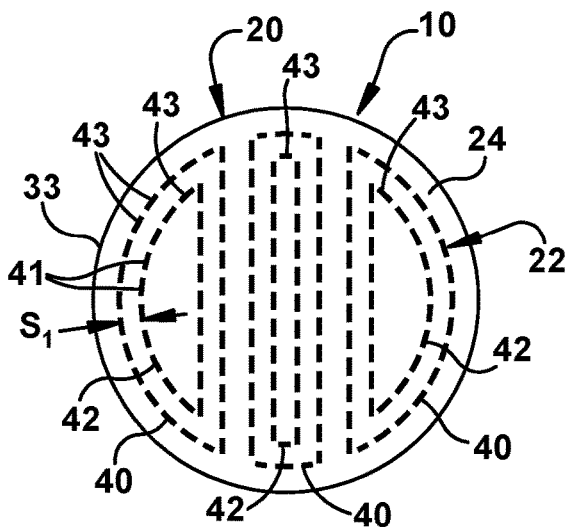
Fig. 3A        Fig. 3B
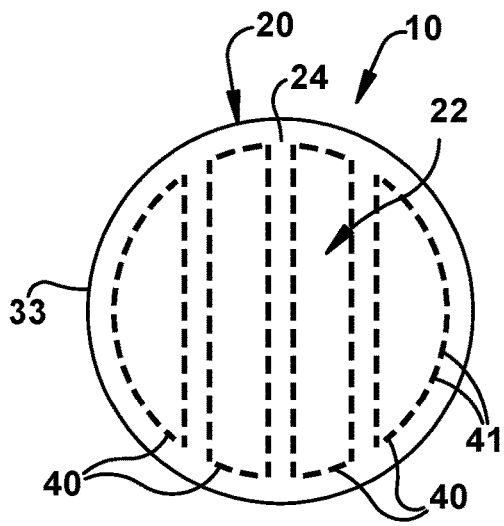
Fig. 3C

Krakow stitch/ Post     Synthes Screw/ Washer     Biotenodesis Screw

|  | 6PGA | 6PLA | Native |
|---|---|---|---|
| Krakow Post | 399.93 | 401.02 | 187.70 |
| Synthes Screw | 371.98 | 379.64 | 146.66 |
| Biotenodesis Screw | 416.54 | 582.09 | 211.22 |

REINFORCED TISSUE GRAFT

RELATED APPLICATION

This application is a divisional of U.S. Ser. No. 12/934,791, filed Sep. 27, 2010, which is a 371 of International Patent Serial No. PCT/US2009/038570, filed Mar. 27, 2009, which claims priority from U.S. Provisional Application No. 61/040,066, filed Mar. 27, 2008, which is incorporated by reference in its entirety.

TECHNICAL FIELD

The present invention is directed to tissue grafts and, in particular, is directed to a reinforced tissue graft.

BACKGROUND OF THE INVENTION

Current treatment for rotator-cuff tears is to suture the torn tendon back to the bone of the humeral head. The sutures hold the tendon in contact with the bone, preferably long enough for the tendon to heal to the bone and form a bridge that will re-establish the tendon-bone connection and restore normal function. The sutures that are used possess sufficient tensile strength to retain the tendon and bone together during the healing process. However, the tendon is a fibrous tissue that can be torn by the sutures. The sutures can align with the fascicular structure of the tendon and tear through it under sufficient tensile force undoing the surgical repair before tendon-to-bone healing is complete. The sutures can also tear through the bone under sufficient force, particularly in older subjects who form the bulk of rotator-cuff-tear patients and whose bones tend to be more osteoporotic.

SUMMARY OF THE INVENTION

The present invention relates to a reinforced, biocompatible tissue graft. The tissue graft includes an extracellular matrix patch (ECM) and a means for reinforcing the graft to mitigate tearing of the graft and/or to improve the fixation retention of the graft when fixed or secured to tissue being treated. The reinforcing means can include a fiber stitched into the ECM patch in a reinforcement pattern. The fiber can be formed from a biocompatible material and have a high modulus of elasticity and failure load. Examples of biocompatible materials that can be used to form the fiber include silk, sericin-free silk, modified silk fibroin, polyesters, such as poly(glycolic acid) (PGA), poly(lactic acid) (PLA), poly(ethylene glycol) (PEG), polyhydroxyalkanoates (PHA) and polyethylene terephthalate (PET), medical grade polyethylene, such as polyethylene (UHMWPE), blends thereof and copolymers thereof, as well as other biocompatible materials that are typically used in forming biocompatible fibers for in vivo medical applications.

Another aspect of the present invention relates to a biocompatible tissue graft that includes a fascia patch and at least one fiber stitched into the patch in a reinforcement pattern to mitigate tearing and/or improve fixation retention of the patch.

Yet another aspect of the present invention relates to a method of constructing a biocompatible tissue graft that includes providing an extracellular matrix patch and stitching at least one fiber into the patch in a reinforcement pattern to mitigate tearing and/or improve fixation retention of the patch.

Still a further aspect of the present invention relates to a method for repairing tissue in a subject that includes administering to the tissue a biodegradable tissue graft. The biocompatible tissue graft includes an extracellular matrix patch and at least one fiber stitched into the patch to mitigate tearing and/or improve fixation retention of the patch.

BRIEF DESCRIPTION OF THE DRAWINGS

The foregoing and other features and advantages of the present invention will become apparent to those skilled in the art to which the present invention relates upon reading the following description with reference to the accompanying drawings, in which:

FIG. 3a is a top view of a tissue graft having a reinforcement means in accordance with yet another embodiment of the present invention;

FIG. 3b is a top view of a tissue graft having a reinforcement means in accordance with yet another embodiment of the present invention;

FIG. 3c is a top view of a tissue graft having a reinforcement means in accordance with yet another embodiment of the present invention;

DETAILED DESCRIPTION

Figure 1:
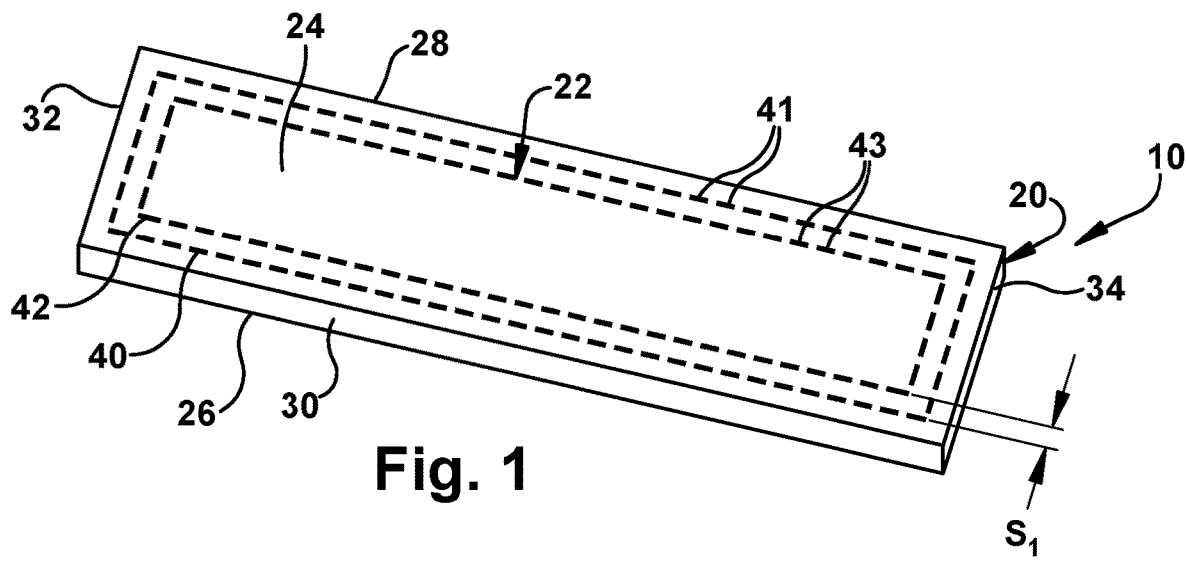
FIG. 1 is schematic illustration of a tissue graft having reinforcement means in accordance with an embodiment of the present invention.

The present invention is directed to tissue grafts and, in particular, is directed to a fiber reinforced tissue graft with improved fixation retention properties. The tissue graft can be used to treat a tissue defect of a subject (e.g., human being), such as a musculoskeletal defect, or in tendon-to-bone repairs (e.g., rotator cuff injury), or soft-tissue repairs, such as the repair of lacerated muscles, muscle transfers, or use in tendon reinforcement. The tissue graft may also be used as a bridging material in a subject in the case where the gap between a tendon and the associated bone is too large to repair conventionally. The tissue graft can be incorporated between the bone-tendon interface and fixed to the bone and tendon to repair a gap or tear.

The tissue graft in accordance with the present invention includes an extracellular matrix (ECM) patch (or ECM) and a reinforcing means. The ECM can be derived from any mammalian ECM, such as fascia, and in particular, fascia lata from humans. The ECM can be derived from other connective tissue materials, such as dermis as long as the ECM is biocompatible with the target site or the tissue injury being treated in the subject or both. The ECM can also be derived, for example, from other tissues and/or other materials, such as collagen, skin, bone, articular cartilage, meniscus, myocardium, periosteum, artery, vein, stomach, large intestine, small intestine, diaphragm, tendon, ligament, neural tissue, striated muscle, smooth muscle, bladder, ureter, abdominal wall fascia, and combinations thereof.

The ECM used to form the tissue graft may be obtained directly from mammalian tissue (such as an autograft, allograft or xenograft). These tissues may be obtained from patients at the time of surgery or a commercial source, such as a tissue bank medical device company. ECM obtained from tissue banks and other commercial sources may be formed using proprietary processing techniques or modified by additional processing techniques before it is used. In one example, these techniques can be used to remove cells and other potentially infectious agents from the ECM.

The reinforcing means can include any structure or material that is applied to the ECM, is capable of mitigating tearing of the graft when the graft is fixed to tissue being treated, and/or is capable of increasing or improving the fixation retention properties of the tissue graft beyond that which is present in a patch of the ECM alone. The fixation retention properties can be tailored to increase the graft's ability to remain secured to anatomic structures, such as bone and soft tissues, when used to treat a tissue defect. The graft may be secured to these anatomical structures by, for example, weaving, screws, staples, sutures, pins, rods, other mechanical or chemical fastening means or combinations thereof. For instance, the graft may be secured to the treated tissue via different suture configurations, such as, massive cuff, mattress stitching and simple suture and different fixation techniques, such as, Synthes screw or Biotenodesis screw fixation and suture anchors with a Krakow stitch.

In one aspect of the invention, the reinforcing means can include a thread or strands of fiber(s) that are stitched in a reinforcement pattern in the ECM patch. Fiber stitched in a reinforcement pattern can increase the fixation properties of the tissue graft, which will result in a tissue graft having improved mechanical properties for implantation and repair of anatomical defects in a subject. The reinforcement pattern can include any stitch pattern that mitigates tearing and/or improves the fixation retention properties of the tissue graft when administered to a subject being treated. For example, the stitch pattern can include one or more generally concentric, peripheral or cross-hatched stitch patterns.

The fiber can enhance the fixation retention of the tissue graft once stitched into the graft. The fiber can be formed from a biocompatible material that is bioresorbable, biodegradable, or non-resorbable. The term bioresorbable is used herein to mean that the material degrades into components, which may be resorbed by the body and which may be further biodegradable. Biodegradable materials are capable of being degraded by active biological processes, such as enzymatic cleavage.

One example of a biocompatible material that can be used to form the fiber is silk. The silk may include, for example, sericin-free silk fibroin or silk-fibroin modified with a peptide sequence that sequesters growth factors in vivo, such as disclosed in U.S. Pat. No. 6,902,932, which is herein incorporated by reference. The fibers can also be formed from biodegradable polymers including poly(glycolic acid) (PGA), poly(lactic acid) (PLA), poly(lactic-co-glycolic acid) (PLGA), poly(ethylene glycol) (PEG), blends thereof, and copolymers thereof. By way of example, the reinforcing fiber may include a core of PGA surrounded by a sheath of reinforced PLA fibers. The PGA and PLA may be obtained, for example, from Concordia Fibers in Coventry, R.I. Other examples of biocompatible polymers that can be used to form the fiber are resorbable polyesters, such as polyhydroxyalkanoates (PHA), and non-resorbable fibers, such as polyethylene terephthalate (PET) and ultra-high molecular weight polyethylene (UHMWPE). It will be appreciated that the biocompatible fiber can be formed from other biocompatible materials, such as other biocompatible materials that are typically used in forming biocompatible fibers for in vivo medical applications.

Regardless of the material used for the fiber of the reinforcing means, the fiber should exhibit a high modulus of elasticity and a failure load tailored to meet particular design criterion corresponding with in vivo strength requirements of the treated tissue. For example, reinforced patches used for the treatment of large and massive rotator cuffs should exhibit failure loads of greater than about 250 Newtons (N) at a time of implantation, and greater than about 150 N after about one week of implantation in vivo. Alternatively, reinforcing patches used for the treatment of tissues experiencing lower natural loads may be required to exhibit failure loads of about 30 N to about 50 N. It will be understood, however, that the fibers, their stitch design (i.e., reinforcement pattern), or the particular ECM can be tailored to produce failure loads of the fiber-reinforced ECM patch commensurate in scale to any tissue treated within the body.

In an aspect of the invention, the fibers and/or the ECM can be mechanically, chemically or biologically modified to enhance adhesion between the fibers and ECM to further secure the fibers to the ECM. This modification may occur before or after the fibers are incorporated into the ECM. This modification may be performed on a portion of or substantially all of the stitched fibers or the ECM or both. During loading of the tissue graft, the fibers may begin to displace relative to the ECM and may ultimately completely slip out from the ECM and become the primary load bearing components of the reinforced tissue construct. It therefore becomes desirable to mitigate or prevent fiber slippage in order to ensure that usage loads are borne by the entire graft and not just the fibers. Adhesion characteristics of the fibers can be improved by ablation via ultra-violet (UV) or infrared (IR) light, UV cross-linking or chemical cross-linking, plasma etching, ion etching, coating the fibers with microspheres, application of bioadhesives or combinations thereof. These treatments can likewise be performed on the ECM.

In another aspect of the invention, the ECM can be processed to become decellularized. Once decellularized, cells can be seeded into the decellularized ECM that enhance the therapeutic potential of the tissue graft. For example, the ECM can be seeded with a plurality of progenitor cells that become dispersed in the ECM. Examples of progenitor cells are known in the art and can include bone marrow-derived progenitor cells, hematopoietic stem cells, endothelial progenitor cells, mesenchymal stem cells, multipotent adult progenitor cells (MAPCs), embryonic stem cells, stromal cells, stem cells, embryonic stem cells, chondrocytes, osteoblasts, and tenocytes. The progenitor cells can be autologous, allogeneic, xenogeneic or a combination thereof. The progenitor cells can also be genetically modified. Genetically modified cells can include cells that are transfected with an exogenous nucleic acid and that express a polypeptide of interest including, for example, a growth factor, a transcription factor, a cytokine, and/or a recombinant protein.

The ECM can additionally or optionally include at least one biologically active molecule dispersed or seeded therein. Any desired biologically active molecule can be selected for impregnating into the ECM. For example, the biologically active molecule can include enzymes, hormones, cytokines, colony-stimulating factors, vaccine antigens, antibodies, clotting factors, angiogenesis factors, regulatory proteins, transcription factors, receptors, and structural proteins. The biologically active molecule can be chosen based on where the musculoskeletal graft is to be located in the subject or the physiological requirements of the subject or both. For example, if the musculoskeletal graft is used to repair a tendon, the biologically active molecule which is seeded on or into the ECM can be a growth factor such as IGF-I, TGF-β, VEGF, bFGF, BMP or combinations thereof.

Optionally, a high-molecular weight (e.g., greater than about 250 kDa) hyaluronic acid (HA) can be incorporated into the tissue graft prior to, during, or after stitching of the fibers into the ECM. When incorporated into the tissue graft, HA can potentially inhibit the migration of inflammatory cells, induce the migration of non-inflammatory cells, and promote angiogenesis, which would promote integration of the ECM with the underlying host tissues.

The high-molecular weight HA can be cross-linked within the ECM to mitigate diffusion of the HA from the ECM. Cross-linked, high-molecular-weight HA can be retained in ECM for extended periods in vitro. An example of a cross-linked HA material that can be used in this application is prepared by substituting tyramine moieties onto the HA chains and then linking tyramines to form dityramine linkages between HA chains, effectively cross-linking or gelling the HA into the ECM. Examples of dityramine-cross-linked HA composition and chemistry are disclosed in U.S. Pat. No. 6,982,298 and U.S. Application Publications Nos. 2004/0147673, 2005/0265959, and 2006/0084759, which are herein incorporated by reference. The tyramine-substitution rate on the HA molecules may be about five percent based on available substitution sites as disclosed in the aforementioned publications.

TS-HA can be impregnated into the ECM, and then immobilized within ECM by cross-linking of the tyramine adducts to form dityramine linkages, thereby producing a cross-linked HA macromolecular network. The TS-HA can be impregnated into the ECM prior to or after stitching the ECM.

The TS-HA can be used to attach fibronectin functional domains (FNfds) to the ECM in order to further promote healing, cell migration, and anti-inflammatory capabilities. FNfds possess the ability to bind essential growth factors that influence cell recruitment and proliferation (e.g., PDGF-BB and bFGF). The FNfds may, for example, constitute fibronectin peptide "P-12" with a C-terminal tyrosine to allow it to be cross-linked to TS-HA.

One example of a tissue graft in accordance with the present invention is illustrated in FIG. 1. The tissue graft 10 includes a reinforced ECM patch or strip that can be used to augment a tendon or muscle repair to bone in, for example, a rotator cuff injury. The tissue graft 10 includes an ECM patch 20 and a means 22 for reinforcing the patch.

The patch 20 is illustrated as having a generally rectangular strip shape (e.g., about 5 cm long by about 2 cm wide) although the patch can have other shapes, such as an elliptical shape, a circular shape, a square shape, etc. (e.g., FIGS. 2, 3, 4). The patch 20 includes a top surface 24 and a substantially parallel bottom surface 26 spaced from the top surface. A first side 28 and second side 30 connect the top surface 24 to the bottom surface 26. The first and second sides 28, 30 extend generally parallel to one another. The patch 20 further includes a front surface 32 and rear surface 34 which connect the first side 28 to the second side 30. The front and rear surfaces 32, 34 extend generally parallel to one another.

The reinforcing means 22 can include at least one fiber disposed or provided within the patch 20 by, for example, conventional stitching techniques. By stitching, it is meant that at least one fiber of the reinforcing means 22 is stitched into the patch 20 such that each stitch of the reinforcing means extends between and through both the top surface 24 and the bottom surface 26 of the patch 20 to securely fasten the reinforcing means to the patch.

The reinforcing means 22 may exhibit any reinforcement configuration or pattern that increases the fixation properties of the patch 20. One such configuration is illustrated in FIG. 1 in which first and second fibers 40, 42 are stitched into the patch 20 in geometrically concentric configurations. Additionally or alternatively, the stitch lines of the fibers can be placed further away from the edges of the patch 20 to delay, mitigate, or prevent slipping of the fibers 40, 42 within the patch 20. Although FIG. 1 illustrates two fibers in a geometrically concentric pattern, it will be understood that more or fewer fibers can be stitched into the patch in a geometrically concentric pattern. Additionally, it will be appreciated that additional fibers can be stitched into the ECM patch 20 in other reinforcement patterns.

As shown in FIG. 1, the first fiber 40 can extend substantially parallel to, be spaced inwardly from, the periphery of the patch 20. By way of example, the first fiber 40 can extend substantially parallel to the first and second sides 28, 30 and the front and rear surfaces 32, 34 of the patch 20 such that the first fiber 40 exhibits a generally rectangular configuration. The first fiber 40 can comprise a plurality of interconnected stitches 41. The ends of the fiber 40 may be stitched together (not shown) to form a continuous stitching construction.

The second fiber 42 can extend substantially parallel to the first fiber 40 and be disposed radially inward of the first fiber 40 within the patch 20. In this configuration, the first and second fibers 40, 42 form a generally geometrically concentric construction in a peripheral double pass orientation. The second fiber 42 can comprise a plurality of interconnected stitches 43. The second fiber can be substantially uniformly spaced inward from the first fiber 40 by a gap indicated by "$s_1$". The gap $s_1$ may be, for example, on the order of about 1 mm to about 3 mm (e.g., about 2 mm), although other spacing configurations will be understood. It will be appreciated that although the gap $s_1$ between the fibers 40 and 42 is substantially uniform, the gap $s_1$ may vary depending on reinforcement pattern in which the fibers 40 and 42 are stitched. The ends of the second fiber 42, like first fiber 40, may be stitched together (not shown) to form a continuous stitching construction.

The first fiber 40 and the second fiber 42 can be stitched in the ECM so that the number of stitches per inch is, for example, about 10 stitches per inch to about 20 stitches per inch (e.g., about 15 stitches per inch). Generally, the more stitches per inch, the greater the strength of the reinforcing means 22 and the fixation retention properties of the tissue graft 10. In some examples, however, it may be desirable to use less stitches per inch to avoid excessive needle penetrations in the ECM 20, which may potentially weaken the tissue graft 10.

Figure 2:
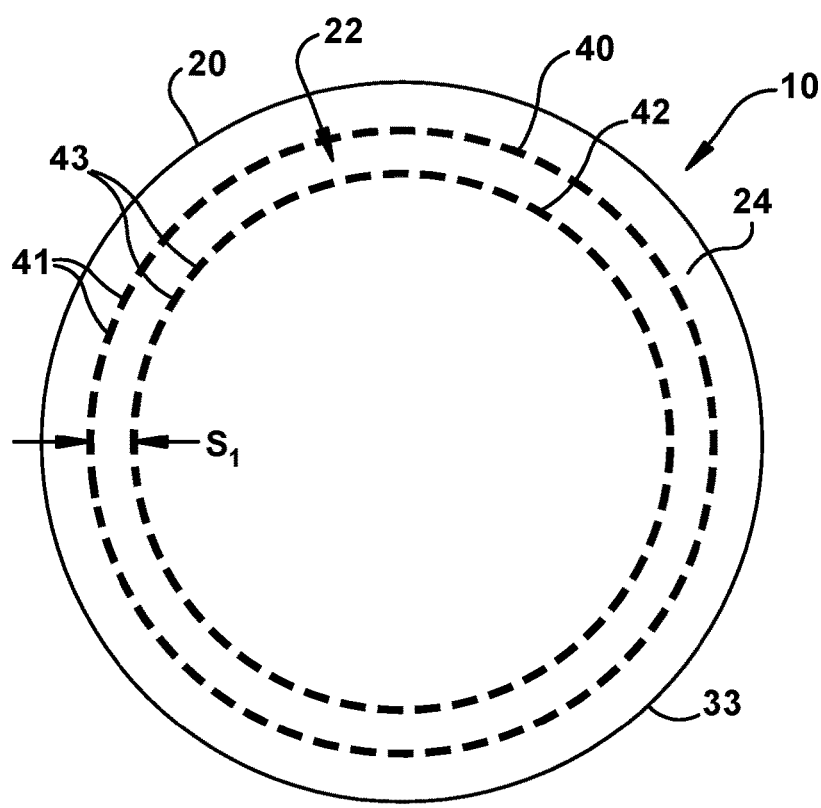
FIG. 2 is a top view of a tissue graft having a reinforcement means in accordance with another embodiment of the present invention.

Other examples of concentric reinforcement stitch patterns or configurations are illustrated in FIG. 2 and FIGS. 3A-3C. The configurations in FIG. 2 and FIGS. 3A-3C are similar to the configuration of FIG. 1, except that in FIG. 2 the patch 20 is substantially circular and therefore the reinforcing means 22 is provided in the patch in a generally circular configuration or orientation. FIG. 2 illustrates one example of a patch 20 that includes generally concentric reinforcement means 22 in a peripheral double pass orientation. The reinforcement means 22 includes a first fiber 40 that comprises a plurality of interconnected stitches 41 and a second fiber 42 that comprises a plurality of interconnected stitches 43. The first fiber 40 can extend substantially parallel to, and be spaced inwardly from, a peripheral surface 33 of the patch 20 such that the first fiber has a generally circular configuration. The second fiber 42 can extend substantially parallel to the first fiber 40 and be disposed radially inward of the first fiber within the patch 20. In this configuration, the first and second fibers 40, 42 form a generally concentric construction.

FIG. 3A illustrates another example of the reinforcing means 22 comprising two concentric patterns 43. Each concentric pattern 43 includes a first strand 40 that comprises a plurality of interconnected stitches 41 and a second strand 42 that comprises a plurality of interconnected stitches 43. Each first fiber 40 can extend substantially parallel to, and be spaced inwardly from, a peripheral surface 33 of the patch 20 such that each first fiber has a generally circular configuration. Each second fiber 42 can extend substantially parallel to the first fiber 40 and be disposed radially inward of the first fiber within the patch 20. In this configuration, each pair of first and second fibers 40, 42 form a generally concentric construction. Although the two concentric patterns 43 are illustrated as being substantially semi-circular, it will be understood that each concentric pattern may exhibit alternative constructions such as, for example, rectangular (e.g., in a two rectangle double pass orientation), elliptical, triangular or combinations thereof within the spirit of the present invention.

FIG. 3B illustrates another example of the reinforcing means 22 comprising three concentric patterns 43. Each concentric pattern 43 comprises a first strand 40 comprising a plurality of interconnected stitches 41 and a second strand 42 comprising a plurality of interconnected stitches 43. Each first fiber 40 can extend substantially parallel to, and be spaced inwardly from, a peripheral surface 33 of the patch 20 such that each first fiber has a generally circular configuration. Each second fiber 42 can extend substantially parallel to the first fiber 40 and be disposed radially inward of the first fiber within the patch 20. In this configuration, each pair of first and second fibers 40, 42 form a generally concentric construction. It will be understood that each concentric pattern may exhibit any constructions such as, for example, rectangular (e.g., in a three rectangle double pass orientation), elliptical, triangular, semi-circular, circular or combinations thereof within the spirit of the present invention.

FIG. 3C illustrates yet another example of a reinforcing means reinforcing means 22 that includes a plurality of first strands 40, which comprise a plurality of interconnected stitches 41 but without or free of concentric second strands 42. In particular, the first strands 40 may comprise four substantially parallel and elliptical discrete first strands. Although the four first strands 40 are illustrated as being substantially elliptical, it will be understood that each first strands may exhibit alternative constructions such as, for example, rectangular (e.g., in a four rectangle single pass orientation), semi-circular, circular, triangular or combinations thereof within the spirit of the present invention. It will also be understood that one or more of the first strands could have a geometrically concentric pattern with a second strand within the spirit of the present invention.

Figure 4A:
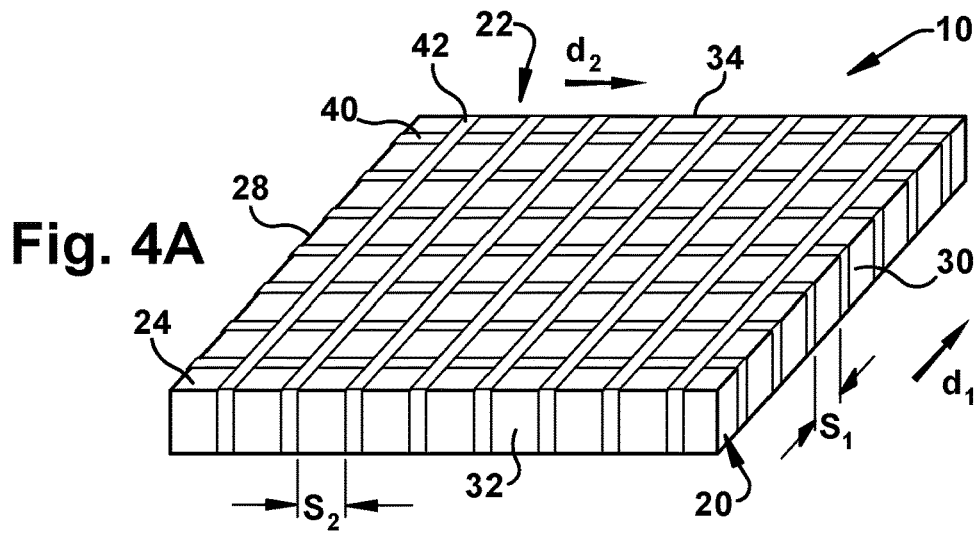
FIG. 4a is a schematic illustration of a tissue graft having a reinforcement means in accordance with yet another embodiment of the present invention.

FIG. 4A is a schematic illustration of a tissue graft 10 that includes an ECM patch 20 and a reinforcing means 22 in accordance with another example of the invention. The reinforcing means 22 includes a plurality of first fibers 40 and a plurality of second fibers 42 stitched in a cross-hatched pattern across the patch 20 and between the first and second sides 28, 30 and the front and rear surfaces 32, 34. Although FIG. 4A illustrates six first fibers 40 and eight second fibers 42, it is understood that more or less of each fiber may be utilized in accordance with the present invention. The first fibers 40 can extend in a first direction, indicated by "$d_1$", across the top surface 24 of the patch 20 from the first side 28 to the second side 30. Each of the first fibers 40 can extend parallel to one another and be spaced apart by a gap indicated by "$s_1$". The gap $s_1$ may be, for example, on the order of about 1 mm to about 3 mm, although other spacing configurations will be understood. The gap $s_1$ may be uniform or may vary between first fibers 40.

The second fibers 42 can extend in a second direction, indicated by "$d_2$", across the top surface 24 of the patch 20 from the front surface 32 to the rear surface 34. The directions "$d_1$" and "$d_2$" in which the first and second fibers 40, 42 extend may be configured such that the first fibers and the second fibers are oriented perpendicular to each other. Each of the second fibers 42 can extend parallel to one another and be spaced apart by a gap indicated by "$s_2$". The gap $s_2$ may be, for example, on the order of about 1 mm to about 3 mm, although the gap can have other spacing configurations. The gap $s_2$ may be uniform or may vary between second fibers 42. The second fibers 42 are disposed in an overlying fashion relative to the first fibers 40 such that the first fibers are disposed between the top surface 24 of the patch 20 and the second fibers. The second fibers 42, however, could alternatively be disposed between the top surface 24 of the patch 20 and the first fibers 40.

Figure 4B:
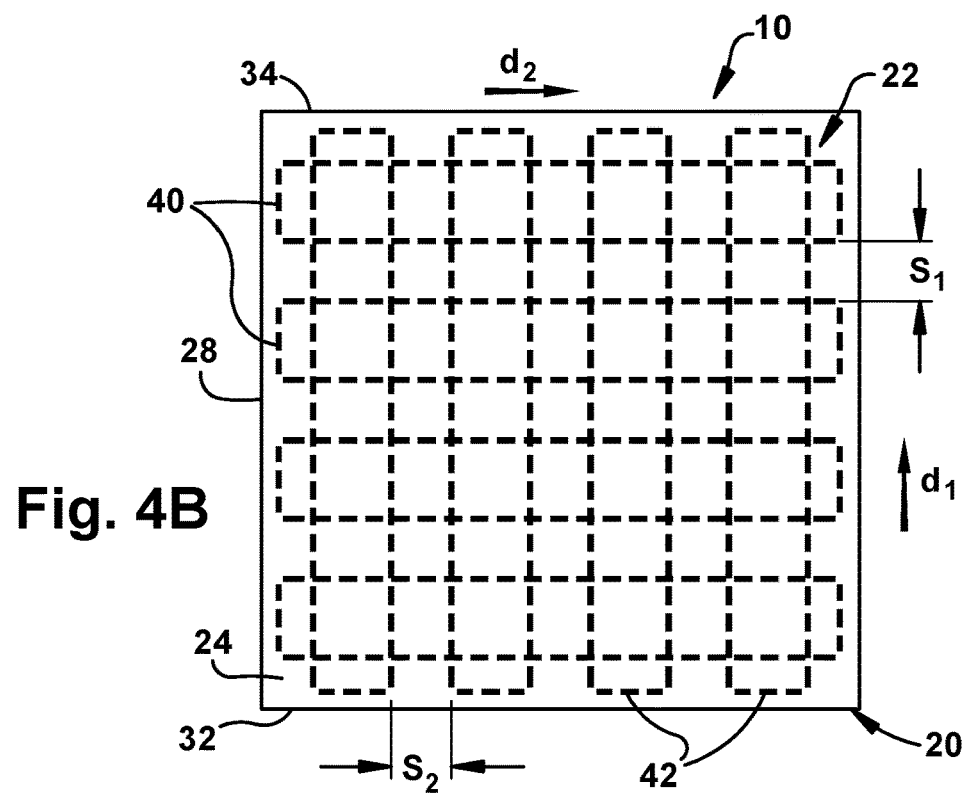
FIG. 4b is a top view of a tissue graft having a reinforcement means in accordance with yet another embodiment of the present invention.

FIG. 4B illustrates that the reinforcing means 22 comprises a plurality of first fibers 40 and a plurality of second fibers 42 stitched in a cross-hatched pattern across the patch 20 and between the first and second sides 28, 30 and the front and rear surface 32, 34. Although FIG. 4B illustrates four first fibers 40 and four second fibers 42, it is understood that more or less of each fiber may be utilized in accordance with the present invention. Each of the first fibers 40 extends from the first side 28 to the second side 30 of the patch 20. Each of the second fibers 42 extends from the front surface 32 to the rear surface 34 of the patch 20. The ends of the first fibers 40 and the ends of the second fibers 42, respectively, may be stitched together (not shown) to form a continuous stitching construction.

The second fibers 42 are disposed in an overlying fashion relative to the first fibers 40 such that the first fibers are disposed between the top surface 24 of the patch 20 and the second fibers. The second fibers 42, however, could alternatively be disposed between the top surface 24 of the patch 20 and the first fibers 40. Although the first and second fibers 40, 42 are illustrated as having a substantially rectangular shape (e.g., a rectangular cross-hatch orientation), it will be understood that the first fiber 40 and/or the second fiber 42 may exhibit alternative constructions such as elliptical, semi-circular, circular, triangular or combinations thereof within the spirit of the present invention.

The tissue graft of the present invention can be used in tissue engineering and musculoskeletal repair, such as rotator cuff repair, but is not restricted to musculoskeletal applications. The graft may be administered to a subject to mechanically and biologically augment the repair by placing it over a tendon-bone repair or interpositionally grafting a rotator cuff tendon defect. It will be appreciated that similar methods and materials as described herein could also be adapted to other tendon-to-bone repairs, soft-tissue repairs, such as the repair of lacerated muscles, muscle transfers, spanning a large muscle defect, or use in tendon reinforcement. These applications require secure connections between the graft 10 and the anatomical site. Fixation techniques to soft tissue using conventional or novel suture methods, or the Pulvertaft weave technique (M. Post, J Shoulder Elbow Surg 1995; 4:1-9) may be utilized in accordance with the present invention. Fixation techniques to bone using conventional or novel suture methods, anchors, screws, or plates may be utilized in accordance with the present invention.

The graft 10 may also serve as a delivery platform for the future investigation of any number of biologic strategies aimed to enhance muscular skeletal repair, e.g., rotator cuff healing. Furthermore, the graft 10 could be effective for other needs in the field of surgical reconstruction, including ligament reconstruction, bowel and bladder reconstruction, abdominal wall repair, and tendon reconstruction in the setting of post-surgical repair failure, trauma and segmental defects. The following examples are illustrative of the principles and practice of this invention. Numerous additional embodiments within the scope and spirit of the invention will become apparent to those skilled in the art.

Example 1

Figure 5A:
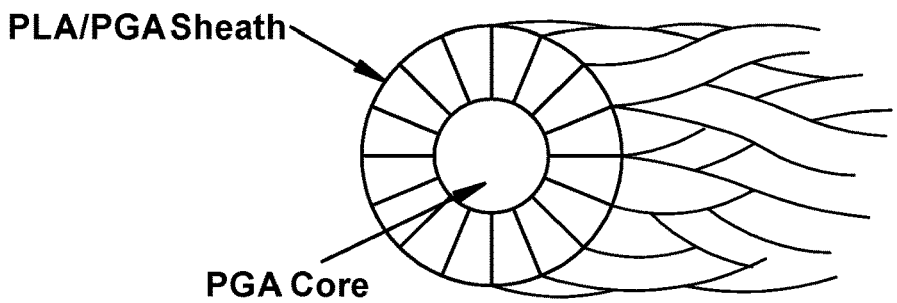
FIG. 5a is a schematic illustration of a fiber of a tissue graft in accordance with yet another embodiment of the present invention.

In this example, two groups were investigated: Group I-Control—Native (unreinforced) fascia and Group II-Experimental—reinforced fascia. The fascia was reinforced using a biodegradable polymer braids as the reinforcing material. Polymer braids used were made of poly lactic acid (PLA) and poly glycolic acid (PGA). PLA and PGA are the most widely researched polymers in the field of tissue engineering. Since PGA degrades more rapidly than PLA, the present example uses polymer braids having PGA as a core and a combination of PLA/PGA as a sheath (FIG. 5A). Two tests were used to verify the efficacy of stitching as a method of reinforcement with polymer braids, namely, uniaxial tension test and multi directional loading using a modified Ball burst test.

All allograft human fascia lata were obtained from the Musculoskeletal Transplant Foundation in Edison, N.J. (donor age 18-55 years). All PGA and PLA braids used for reinforcing the fascia were obtained from Concordia Fibers, Coventry, R.I.

Uniaxial Suture Retention Test

A sample size of (n=10) unreinforced patches were used as the control. Each consisted of 2 cm wide×5 cm long strips of ECM hydrated for 20 minutes in saline solution and maintained at room temperature. The unreinforced patches were tested with either one mattress (n=5) or one Mason Allen suture (n=5) placed 5 mm away from the 2 cm wide edge. A template was created to assure uniformity in the placement of the sutures. The two sutures were tied over a tubular rod mounted on the cross head of a MTS 5543 table top system.

A sample size of (n=7) reinforced fascia were used to test the ability of stitching with two types of PLA/PGA braid to improve the suture retention strength over unreinforced fascia. This sample size was selected due to the preliminary nature of the study. Each reinforced patch consisted of fascia 2 cm wide×5 cm long reinforced with a polymer braid having a sheath of 4PLA and 4PGA with (n=2) and without (n=5) a 2PGA core. The reinforced patches were tested with two simple sutures placed 5 mm away from the 2 cm wide edge. The suture retention load was defined as the maximum load attained by the specimen.

Figure 5B:
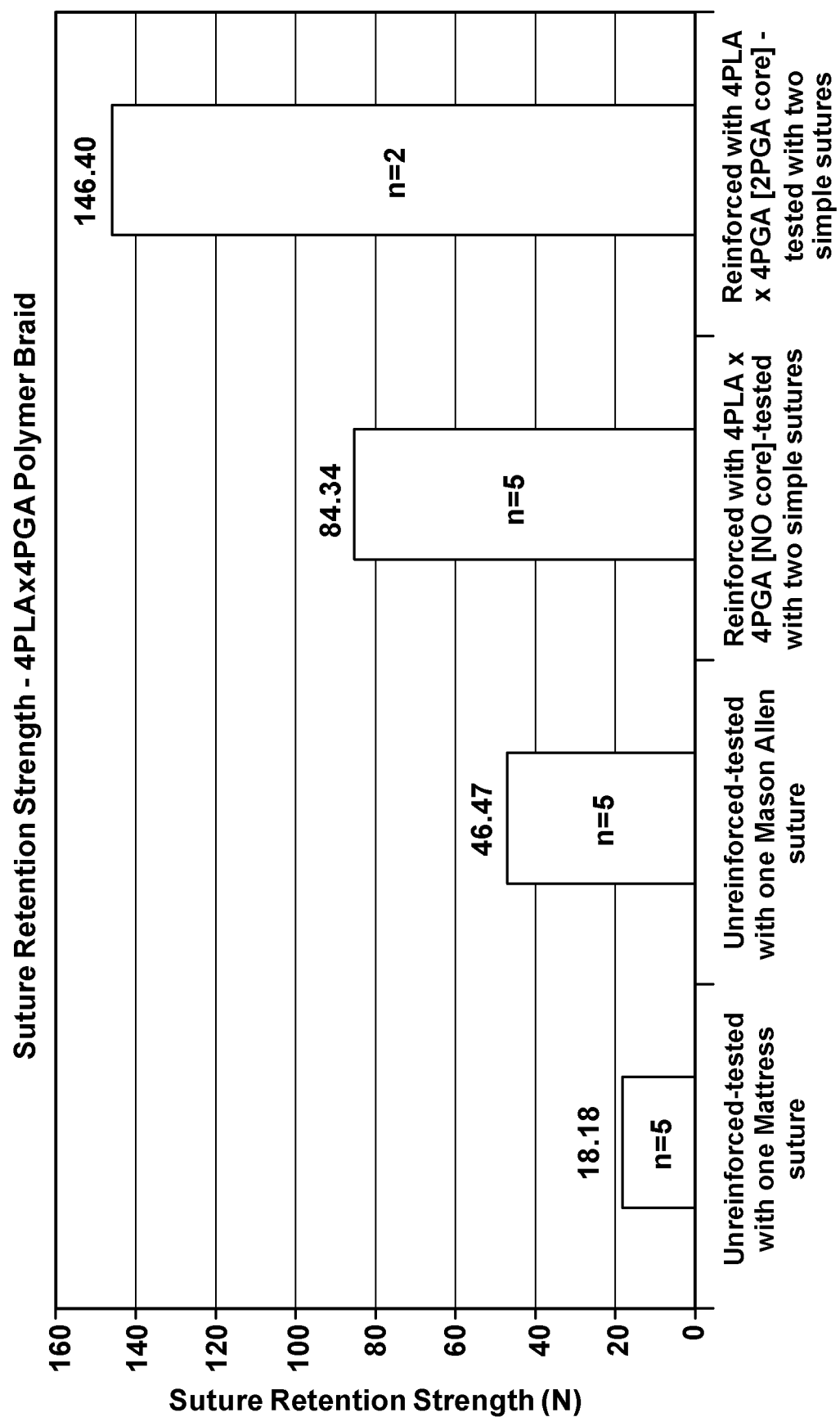
FIG. 5b is a graph illustrating the uniaxial suture retention strength of unreinforced and reinforced tissue grafts.

The results of this test are illustrated in FIG. 5b. FIG. 5b shows that stitching as a reinforcement method has the ability to increase the suture retention strength of fascia. Additionally, the presence of a PGA core in the polymer braid positively impacts the reinforcement by increasing the suture retention strength of the tissue. The suture retention loads obtained with the polymer braids having no PGA core (84 N) were about half the suture retention loads attained with polymer braids having a PGA core (146 N).

Ball Burst Test

Depending on the size, location, and chronicity of the tear in vivo, the graft may be subjected to biaxial tensile forces. Therefore, experiments using a modified Ball Burst test, inspired from the ASTM D3787 Ball Burst test standard used to determine the bursting resistance of knitted fabrics and goods under multi-axial forces, were used to quantify the suture retention strength. In particular, 4 cm diameter discs of the unreinforced and reinforced fascia were hydrated for 20 minutes in saline at room temperature. The hydrated specimens were then sutured to a stainless steel ring (5 cm outer diameter) in a simple suture configuration at 1 cm increments using No. 2 Fiberwire (Arthrex Corporation, Naples, Fla.). The fascia-steel construct was then mounted on a specially designed fixture, which was then mounted on the base of the MTS 1321 system. A polished stainless steel ball having a 1" diameter was attached to the cross head of the MTS system and pushed through the specimen at a constant distraction rate of 6 mm/min. The suture retention load was noted as the maximum load attained by the specimen prior to a 10% or more drop in the peak load.

Figure 6:
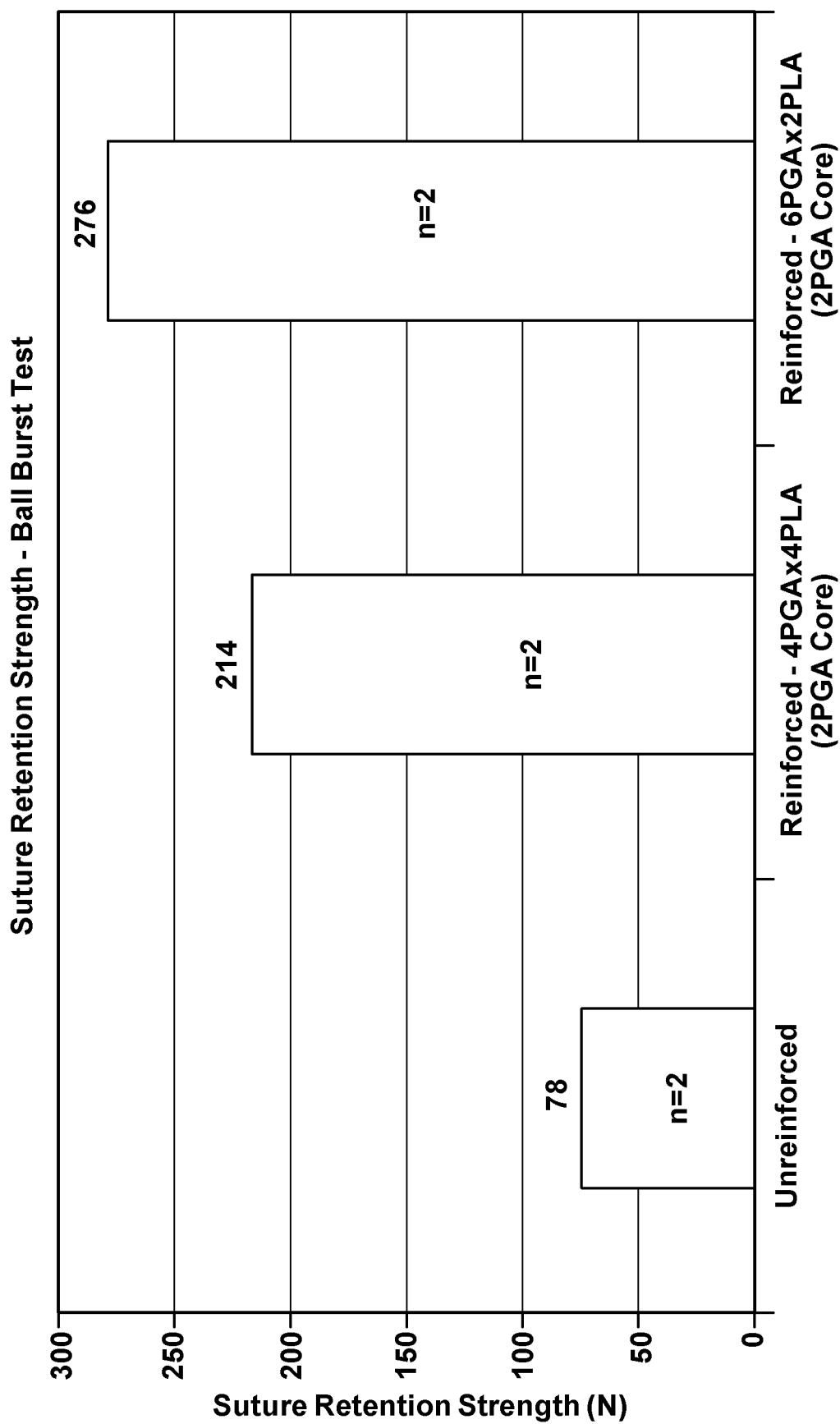
FIG. 6 is a graph illustrating the multi-directional suture retention strength of unreinforced and reinforced tissue grafts.

The results of the Ball Burst test are illustrated in FIG. 6. FIG. 6 shows that even with the Ball Burst test, which is more rigorous than the uniaxial test in that it subjects the specimen to multi-directional loading, the reinforced fascia construct has suture retention strength about 3 to about 4 times greater than unreinforced fascia. FIG. 6 also illustrates that the amount of PGA in the polymer braid directly affects the suture retention strength. This result was expected, as PGA has higher tensile strength compared to PLA.

Example 2

In Vitro Degradation Study

Fascia discs having a diameter of 4 cm were stitched along the periphery using PLA, PGA, and PE polymer braids (n=6 per group). Three specimens per group were allocated to time zero testing and three were subjected to in vitro degradation. For in vitro degradation, the specimens were put in individual beakers containing 100 mL of 1×PBS (pH=7.4) and immersed in a water bath maintained at 37° C.

The 1×PBS solution was checked every day for any signs of contamination and the solution was changed every other day so as to maintain a constant pH of 7.4 throughout the study. At the end of the 21 days the specimens were removed and sutured to a stainless steel ring in simple suture configuration at 1 cm intervals. The suture retention loads of the two groups, time zero and 21 days, were quantified using the modified ball burst test. Failure testing included 10 cycles of preconditioning form 5-15 N at 0.25 Hz followed by load to failure at 30 mm/min.

Figure 7:
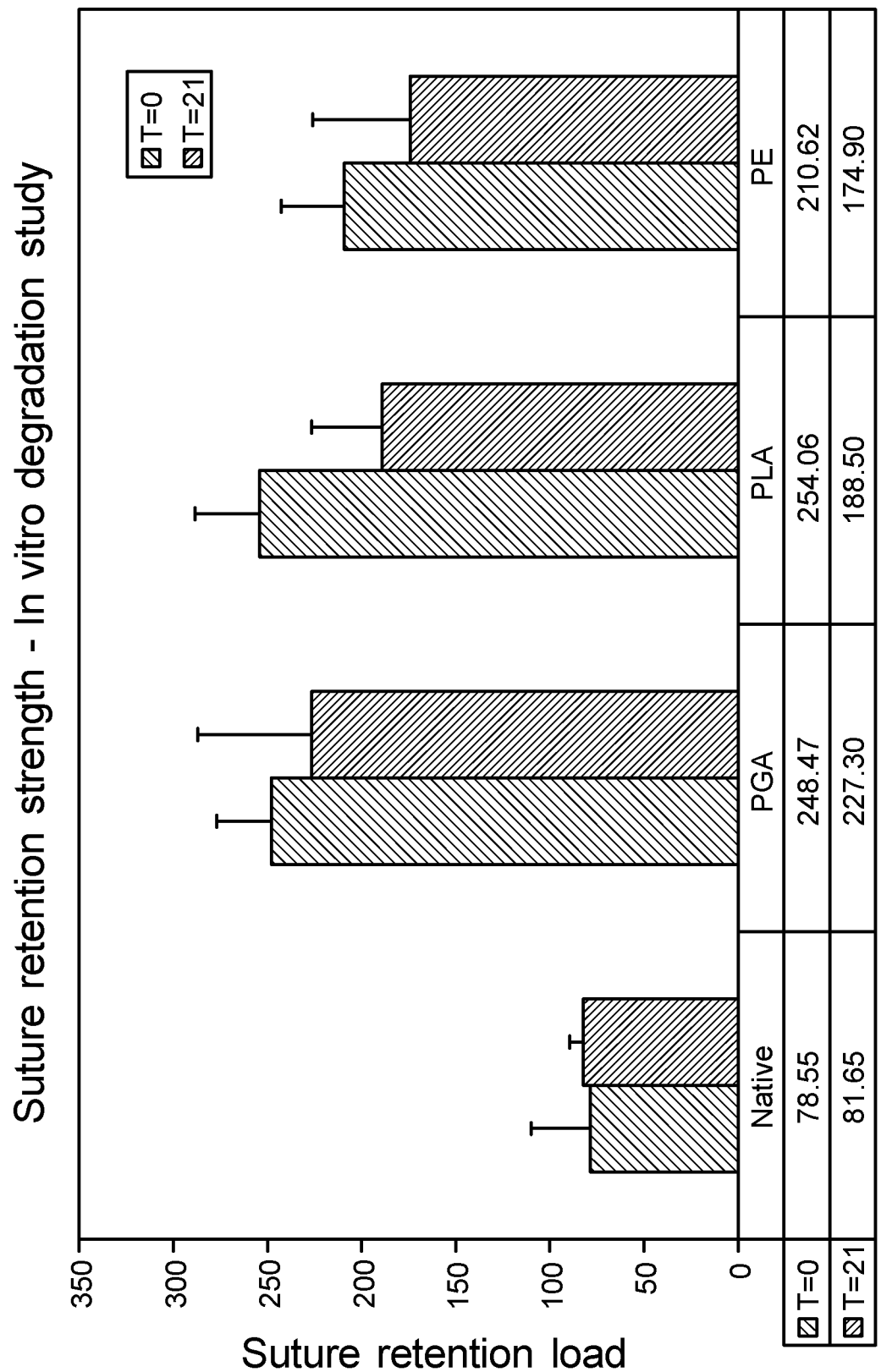
FIG. 7 is a graph illustrating the multi-directional suture retention strength of unreinforced and reinforced tissue grafts before and after 21 days incubation in 1×PBS (pH=7.4) at 37° C.

Suture retention load of fascia stitched with the three polymer braids at the two time points, time zero and 21 days, is shown in FIG. 7. FIG. 7 shows that the suture retention loads for fascia stitched with the three polymer braids is significantly higher than native fascia at both time zero and 21 days. The suture retention load of stitched fascia was not significantly different within a group as a function of time, or between groups at either time point. The data show that stitched fascia significantly increases the suture retention load of fascia and the increase is maintained for at least 21 days in simulated in vivo conditions.

Example 3

Design Configurations

4×4 cm pieces of fascia were stitched using 2-0 commercial silk suture (Harvard Appparatus, Holliston, Mass.) using five stitch configurations: 1) peripheral double pass; 2) 2 rectangle double pass; 3) 3 rectangle double pass; 4) 4 rectangle double pass; and 5) rectangular cross-hatch. The samples were tested using the previously described modified ball burst test and a pseudo side constraint test. For the pseudo side constraint test, the sample was constrained to a stainless steel ring using simple suture configurations and was distracted in uniaxial tension to failure at 30 mm/min.

Figure 8:
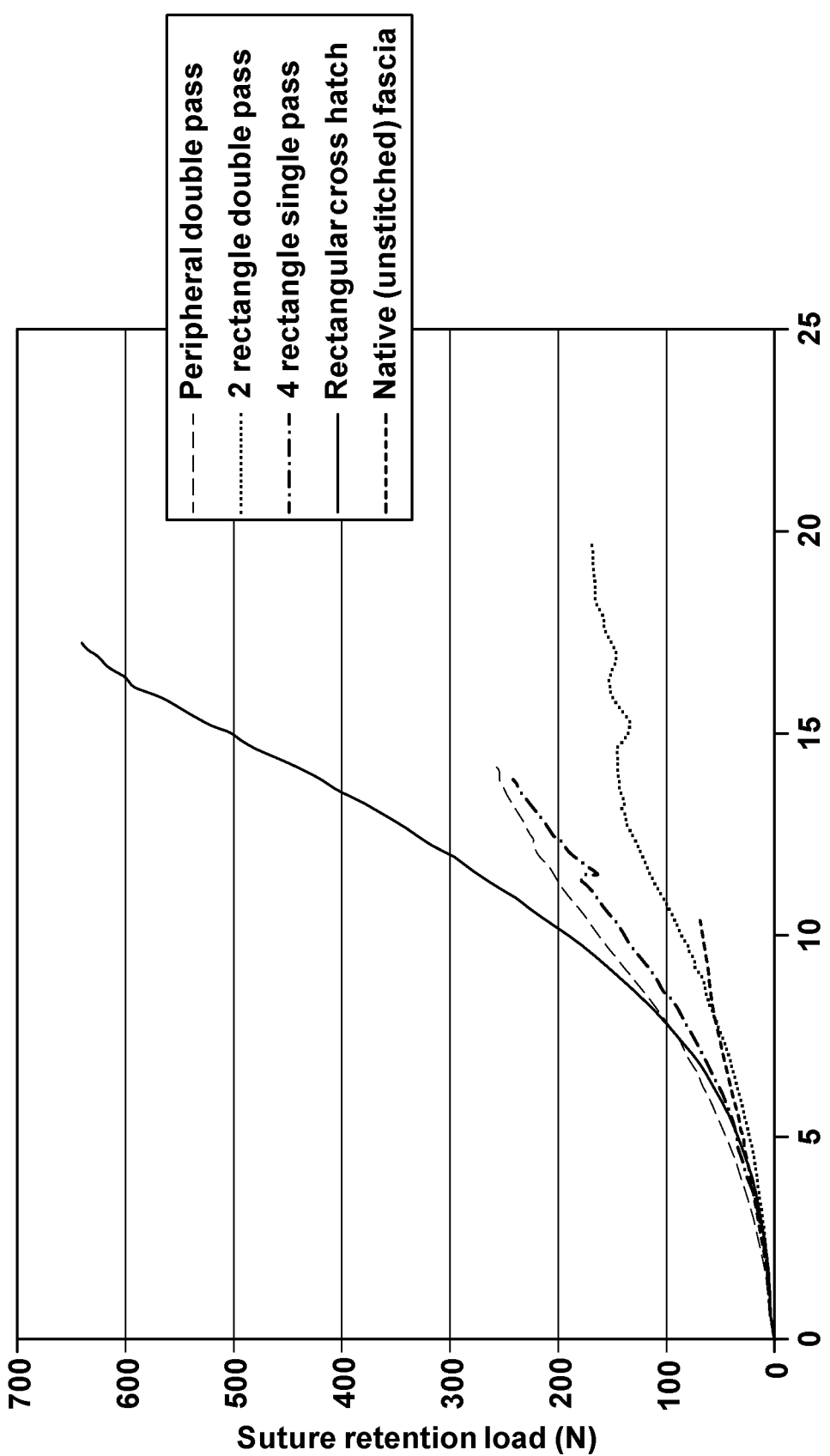
FIG. 8 is a graph illustrating load-displacement plots of unreinforced tissue grafts and tissue grafts reinforced using different stitch designs and tested using a multi-directional ball burst test.
Figure 9:
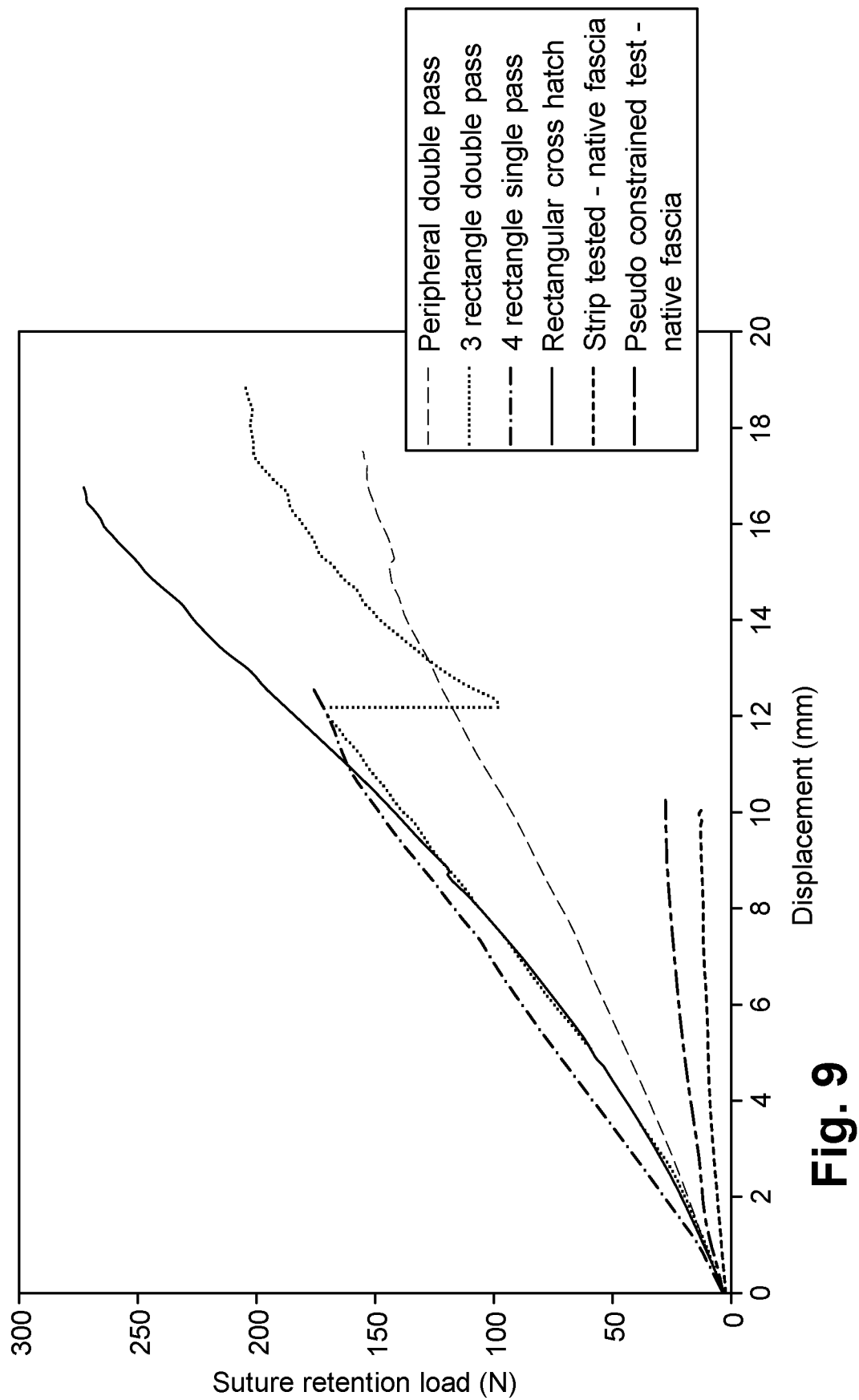
FIG. 9 is a graph illustrating load displacement plots of unreinforced tissue grafts and tissue grafts reinforced using different stitch designs tested in uniaxial tension with side constraint.

The results are illustrates in FIGS. 8-9. Using both test methods, the rectangular cross-hatch stitch pattern had the highest suture retention loads compared to other stitch configurations investigated. These data show that the rectangular cross-hatch stitch pattern will make the mechanical performance of fascia suitable for large to massive rotator cuff tendon repairs.

Example 4

A polymer braid having a 6PLA sheath with 2PGA core (Concordia Medical, Coventry, R.I.) was stitched into strips and patches of human fascia lata ECM. To model in vivo physiologic loading, the suture retention loads were quantified using three different tests: unidirectional pull (FIG. 10), modified ball burst (FIG. 11), and tension with side constraint (FIGS. 12-13). For all tests, load was applied to the samples using #2 Fiberwire simple sutures (Arthrex Corporation, Naples, Fla.).

Specimens were subjected to failure testing using all three types of tests. Failure testing included 10 cycles of preconditioning from 5-15 N at 0.25 Hz followed by constant rate distraction to failure at 30 mm/min. As well, samples were subjected to cyclic fatigue testing (5-150 N, 5000 cycles at 0.25 Hz in a saline bath) using the tension with side constraint test.

Figure 10:
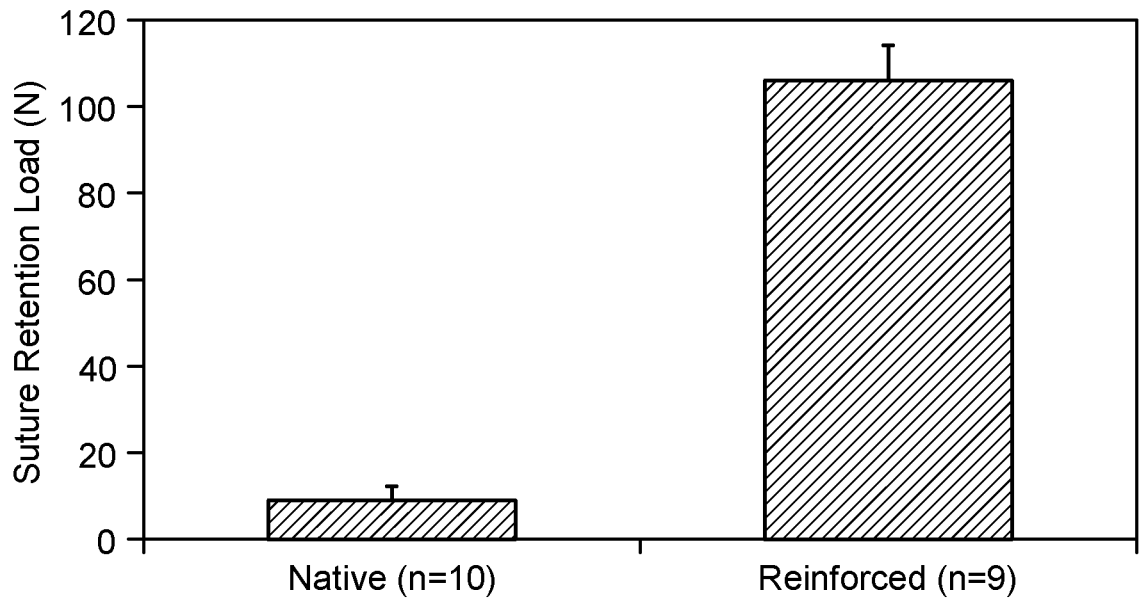
FIG. 10 is a graph illustrating the uniaxial suture retention strength of unreinforced and reinforced tissue grafts using a peripheral stitch design.
Figure 11:
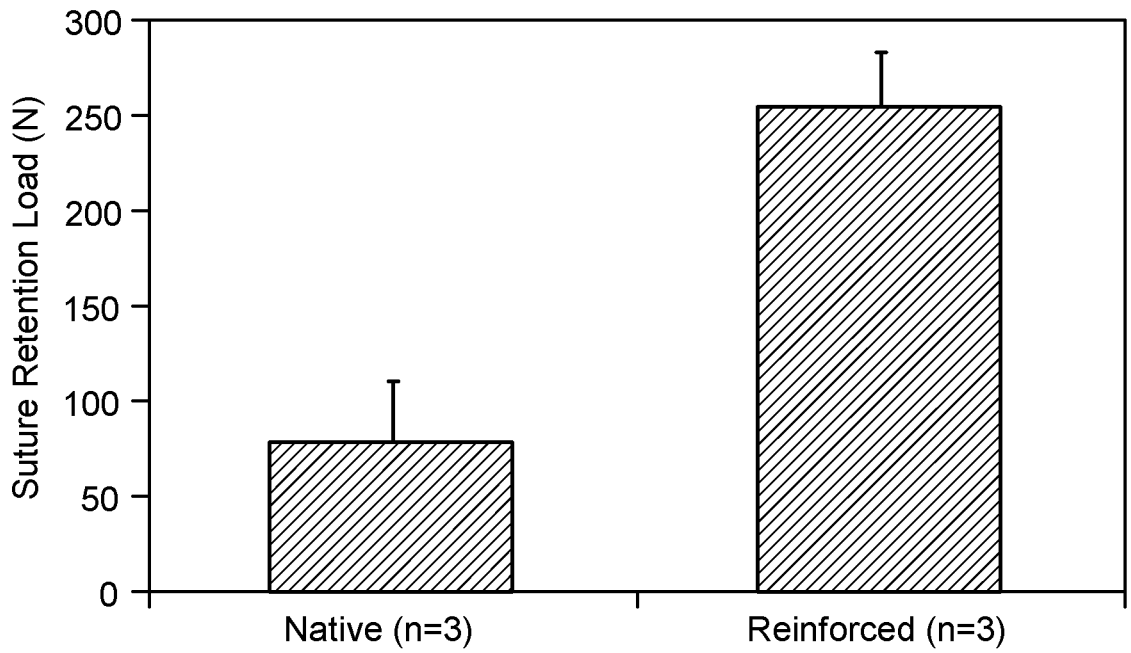
FIG. 11 is a graph illustrating the multi-directional suture retention strength of unreinforced and reinforced tissue grafts using a peripheral stitch design.
Figure 12:
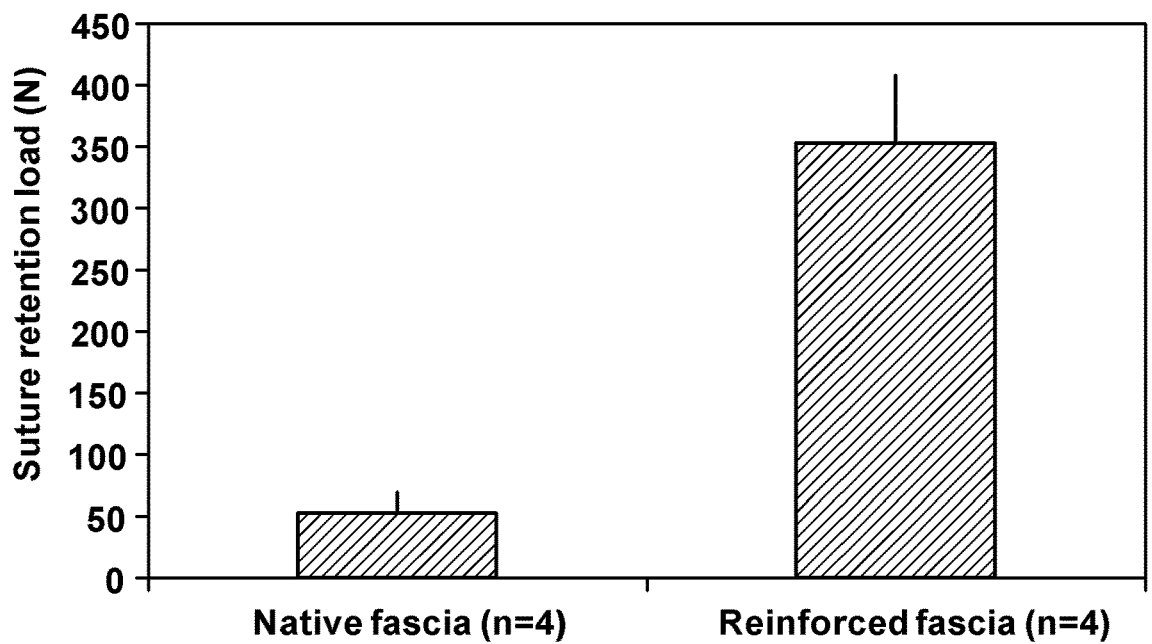
FIG. 12 is a graph illustrating the uniaxial suture retention strength of unreinforced and reinforced tissue grafts using a rectangular cross-hatch stitch design.
Figure 13:
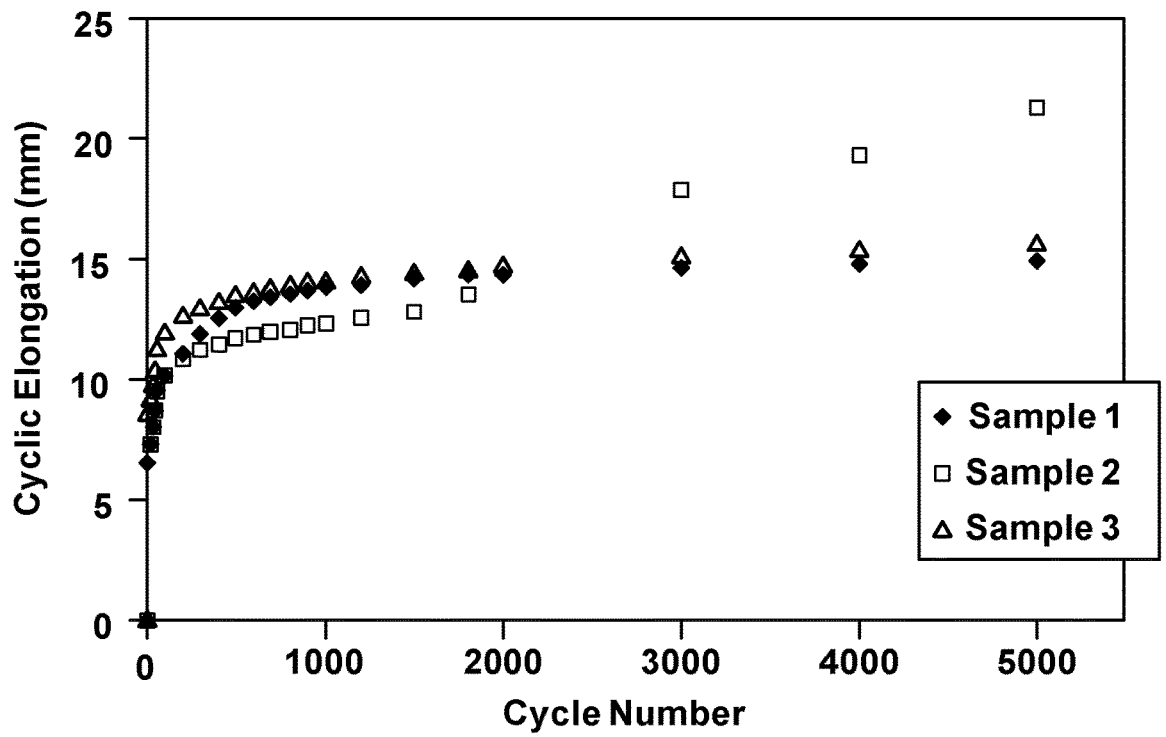
FIG. 13 is a graph illustrating the cyclic elongation during uniaxial fatigue loading of unreinforced and reinforced tissue grafts using a rectangular cross-hatch stitch design.

The results indicate that reinforcing fascia lata ECM with a biodegradable polymer significantly increases its suture retention strength to physiologically relevant loads (>100 N) (FIGS. 10-12). Further, the reinforced patch can resist cyclic fatigue loading at physiologically relevant loads (5-150 N) for up to 5000 cycles (FIG. 13). Hence, reinforced fascia may provide a natural, strong, and mechanically robust scaffold for bridging tendon or muscle defects.

Example 5

Bone Fixation Method

Figure 14:
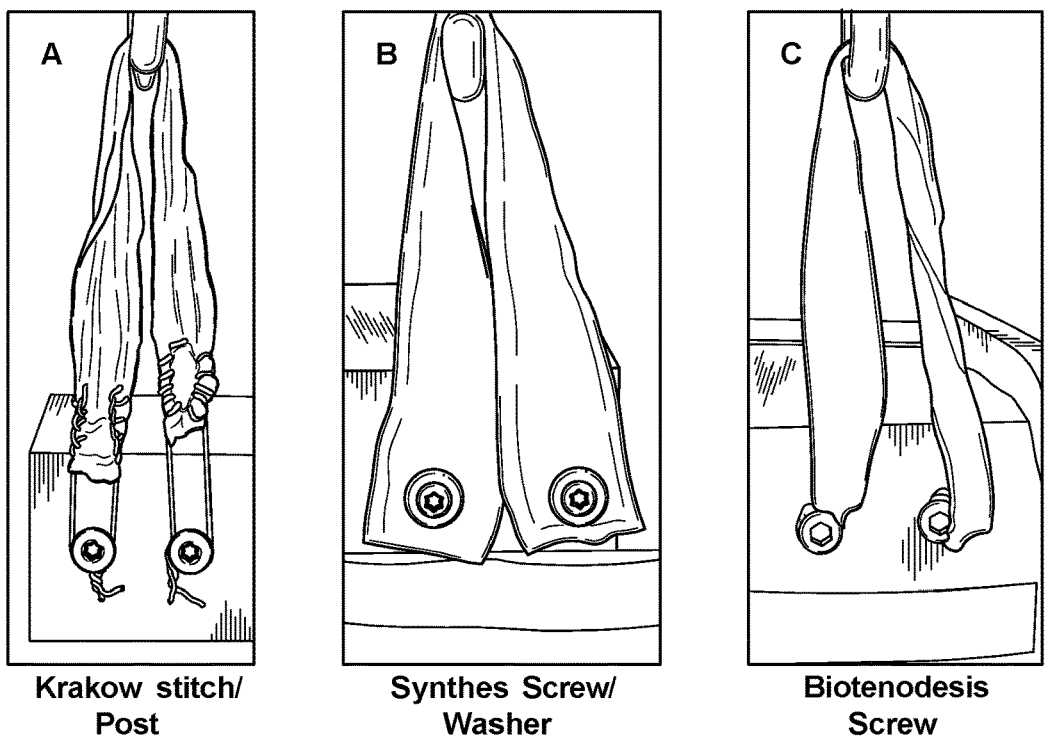
FIG. 14 is a schematic illustration of bone fixation methods for unreinforced and reinforced grafts.

16×1.5 cm pieces of fascia were stitched using a peripheral double pass configuration using 6PGA and 6PLA polymer braids. Reinforced fascia was repaired to Sawbones using the following fixation techniques: 1) Krakow stitch with post (models suture anchor) (FIG. 14A, n=2); 2) Screw and washer fixation (FIG. 14B, n=2); and Biotenodesis interference screw (FIG. 14C, n=2). The samples were tested 100 cycles, 5-50 N at 0.25 Hz and then loaded to failure at 30 mm/min.

Figure 15:
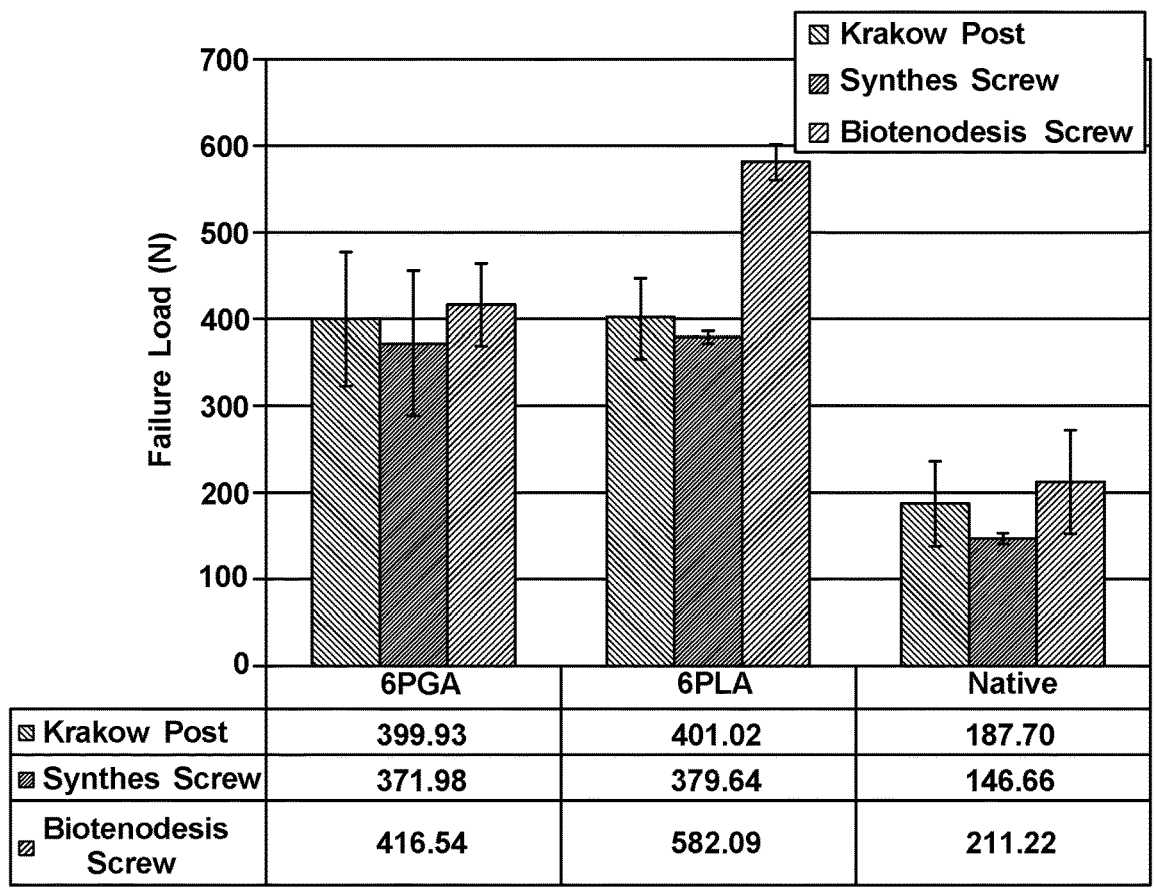
FIG. 15 is a graph illustrating the failure load of unreinforced and reinforced tissue grafts for various bone fixation methods.
Figure 16:
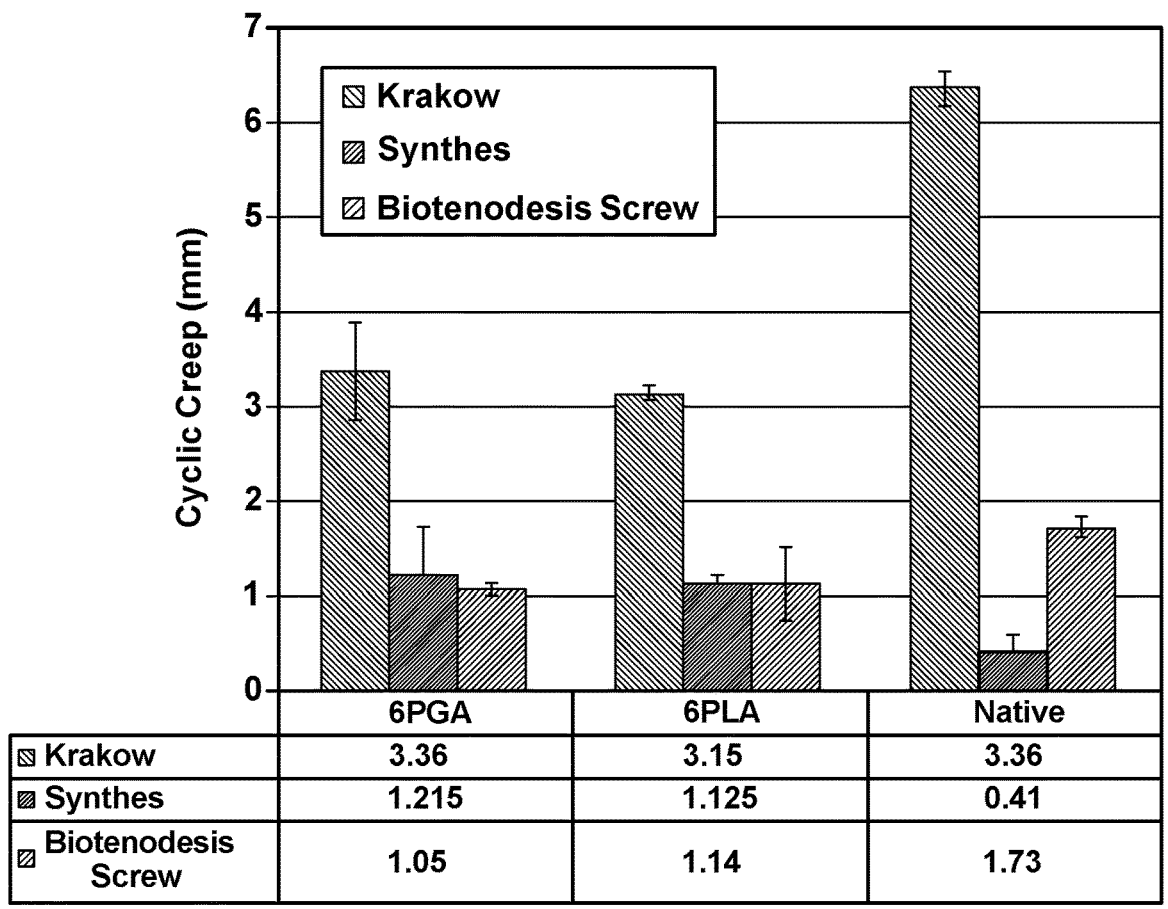
FIG. 16 is a graph illustrating the cyclic creep of unreinforced and reinforced tissue grafts for various bone fixation methods.
Figure 17:
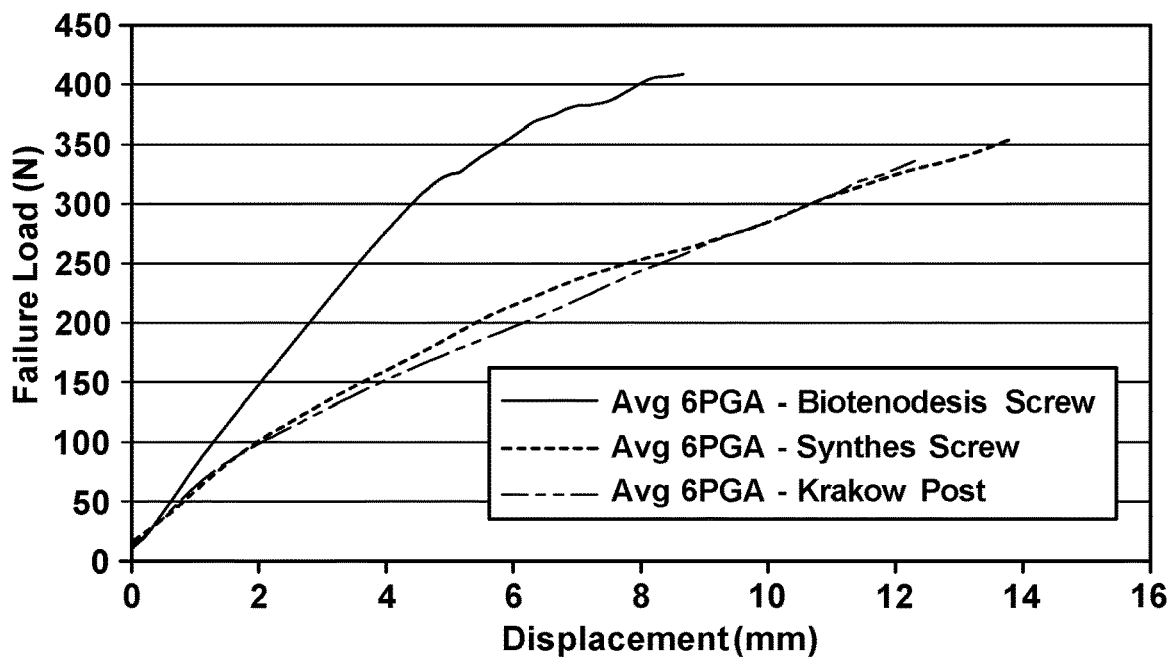
FIG. 17 is a graph illustrating the uniaxial load-displacement curve of reinforced tissue grafts for various bone fixation methods.

The results are summarized in FIGS. 15-17. Failure load is higher in reinforced fascia than native fascia with all bone fixation methods (FIG. 15), and failure load is not different between fixation methods or fiber types tested (FIG. 15). Krakow stitch fixation allows more cyclic creep than the other methods (FIG. 16). Representative load-displacement curves for the failure portion of the test for samples reinforced with PGA fiber are shown in FIG. 17. Biotenodesis screw fixation proved to be the stiffest of the three methods during the failure portion of the test (FIG. 17).

Example 6

Suture Retention Test with Non Resorbable Fibers

The studies were conducted to compare the suture retention load of fascia reinforced with non-resorbable polyesters, sizes 2-0 and 3-0 polyethylene terephthalate (PET) braided suture (Ashaway Twin Mfg. Co., RI) and ForceFiber™ UHMWPE braided suture (Teleflex Medical, MA). Suture retention loads were quantified using the uniaxial suture retention test and compared to fascia reinforced with size 2-0 custom braided PLA suture (Concordia Fibers, RI).

Each 2×5 cm strip was provided with an inner stitch line placed 5 mm away from the edge of the tissue and an outer stitch line placed 3 mm from the edge of the tissue. A template was created to assure uniformity in the placement of the sutures.

The suture retention load, defined as the maximum load attained by the specimen was quantified using a standard pull to failure test with one simple suture. The specimen was preloaded to 2 N and then distracted to failure at a rate of 30 mm/min.

Figure 18:
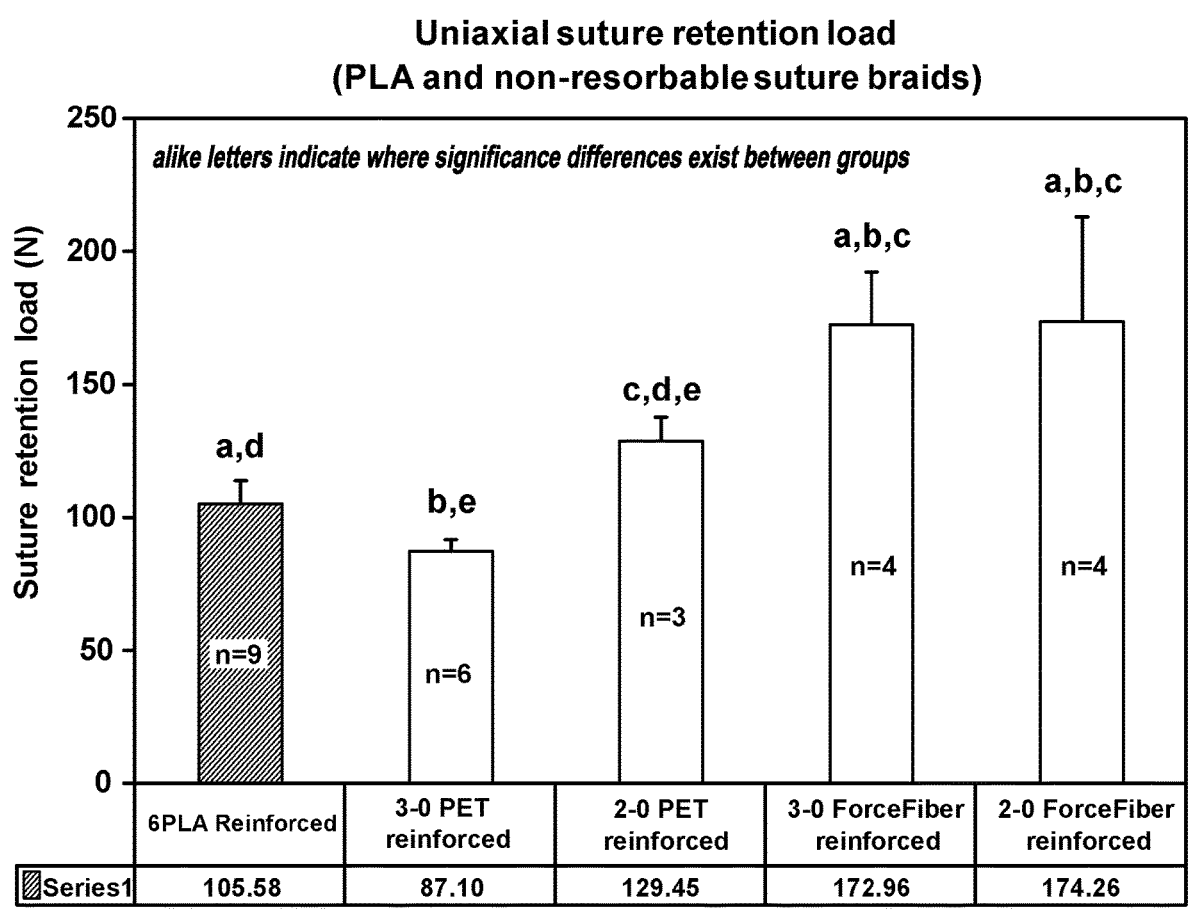
FIG. 18 is a graph illustrating the uniaxial suture retention strength of unreinforced tissue grafts and tissue grafts reinforced with resorbable and non-resorbable fibers.

The results of this test are illustrated in FIG. 18. FIG. 18 shows that stitching as a reinforcement method has the ability to increase the suture retention strength of fascia (compare to unreinforced fascia shown in FIG. 10). Even though different polymer braids have been used, the table clearly indicates an increase in suture retention properties, irrespective of the polymer braid used as the reinforcing material. Additionally, suture retention strength of the fascia reinforced with FORCE FIBER in both sizes was significantly higher compared to fascia reinforced with the PET braided and PLA braided suture materials. No significant difference, however, in suture retention strength was found between 2-0 (174±39 N) and 3-0 (173±20 N) FORCE FIBER reinforced fascia. Further, the 2-0 PET reinforced fascia (129±8 N) had a significantly higher suture retention load compared to the 3-0 PET reinforced fascia (87±5 N) and the PLA reinforced fascia (106±9 N).

Suture Displacement Test

Figure 19:
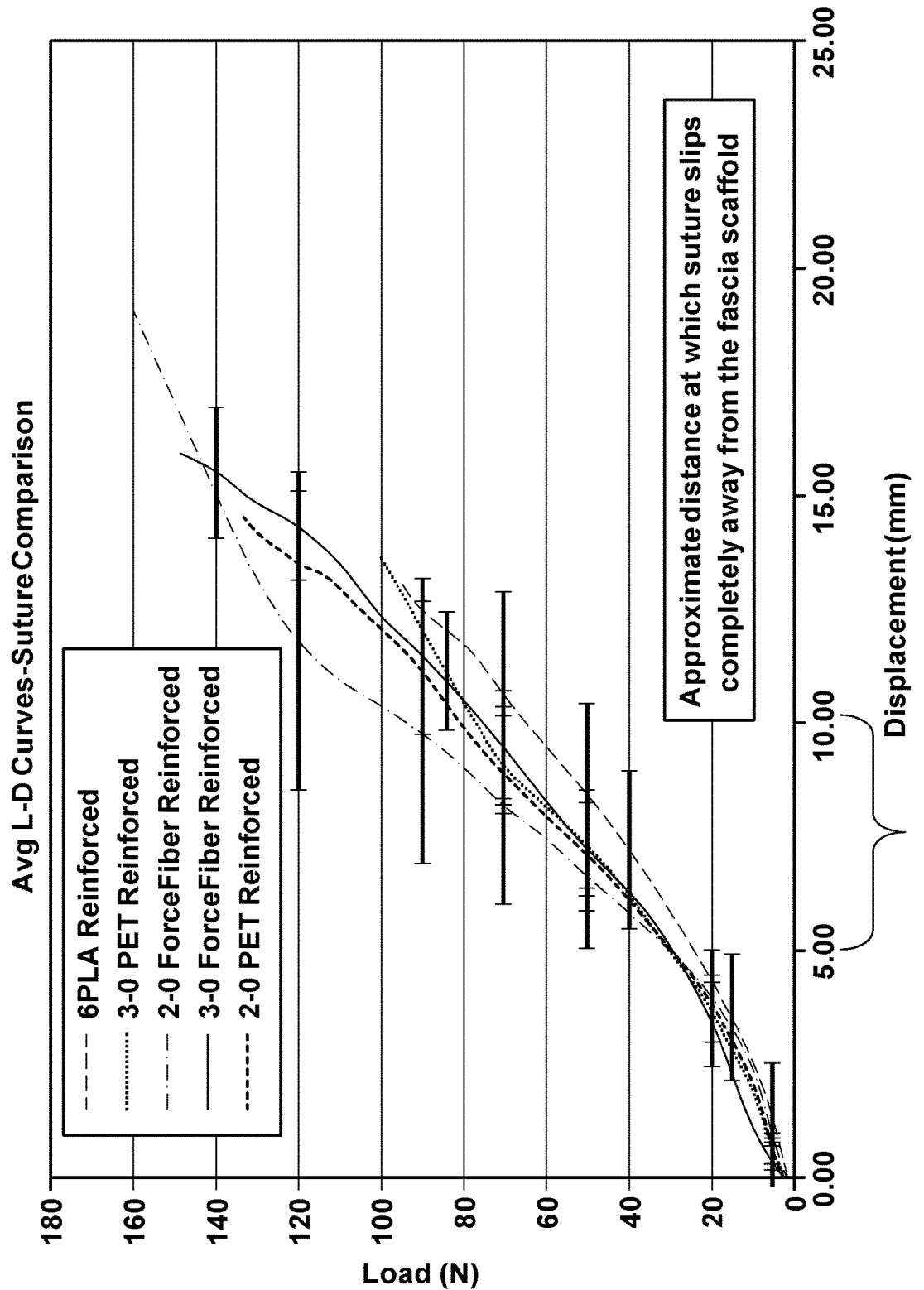
FIG. 19 is a graph illustrating the uniaxial load-displacement curves of tissue grafts reinforced with resorbable and non-resorbable fibers.
Figure 20:
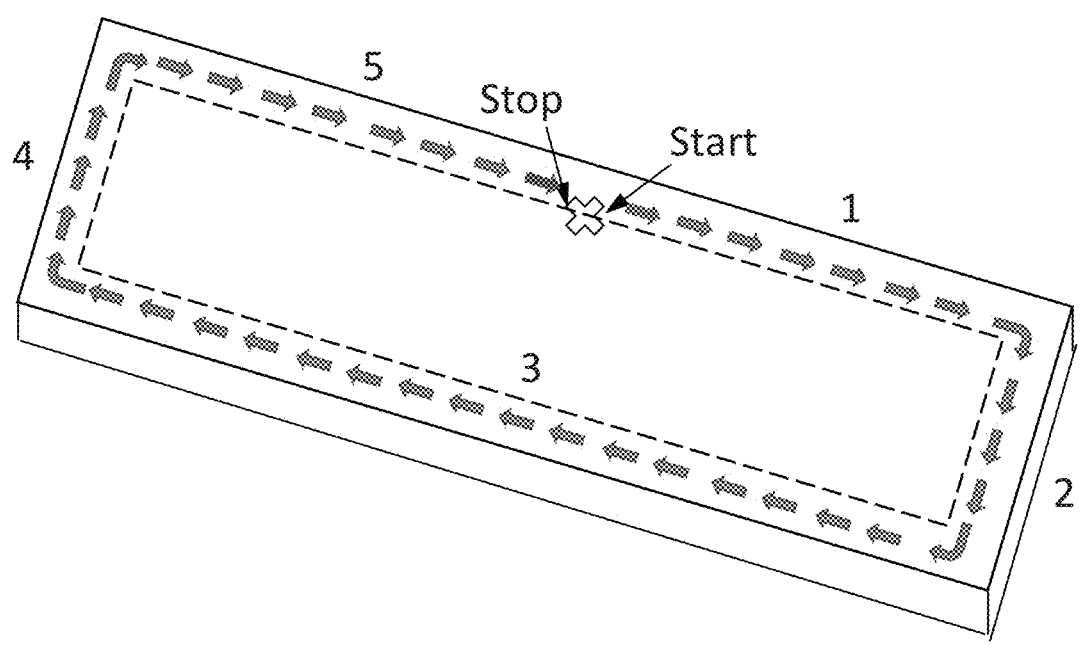
FIG. 20 is a schematic illustration of a tissue graft having a concentric reinforcement means and opposing terminal ends of the fibers stitched together in accordance with yet another embodiment of the present invention.

FIG. 19 gives the average load displacement plots (LD) of 2×5 cm strips of fascia reinforced with 2-0 and 3-0 sized PET braided suture (Ashaway Twin Mfg. Co., RI) and FORCE FIBER UHMWPE braided suture (Teleflex Medical, MA). The LD plot was also generated for fascia reinforced with 6PLA.

The LD plots for fascia reinforced with different suture materials is essentially the same until 5 mm of displacement. Visual inspection suggests that initially both the fibers and fascia matrix are loaded as the fibers slip through the fascia matrix. After about 5 mm of displacement, however, the fibers completely slip out from the fascia matrix and become the primary load bearing components of the reinforced fascia construct.

The complete slippage of fibers from the fascia matrix corresponds to the initial placement of the stitch lines at 5-10 mm from the edge of the fascia patch. After the fiber has completely slipped from the fascia, the maximum load attained by the reinforced fascia construct depends on the ultimate tensile strength and knot breaking strength of the respective fibers used to reinforce the fascia.

For the PET samples, slipping of the fiber at the fiber-fascia interface was followed by breaking of the stitched fiber loop at displacements greater than 5 mm. The FORCE FIBER samples failed when the inner stitch line unraveled in the direction of loading together with pulling along the stitching lines and breaking of the stitched loops.

It may be concluded from the LD plots that 2-0 FORCE FIBER reinforced fascia is stiffer than fascia reinforced with other suture materials. The large error bars seen in FIG. 19 for the 2-0 FORCE FIBER reinforced fascia are due to the divergent behavior of one of the four tested specimens.

Having described the invention, the following is claimed:

1. A biocompatible tissue graft comprising:
   an extracellular matrix (ECM) derived from collagen; and
   a plurality of fibers stitched into the ECM in a concentric reinforcement pattern, each of the fibers comprising the plurality of fibers having opposing terminal ends;
   wherein the plurality of fibers comprises a plurality of interconnected stitches;
   wherein the opposing terminal ends of each of the fibers are stitched together to form a continuous stitching construction;
   wherein the plurality of fibers mitigates tearing and/or improves fixation retention of the graft.

2. The tissue graft of claim 1, wherein the plurality of fibers is disposed radially inward of edges of the graft.

3. The tissue graft of claim 1, wherein the plurality of fibers is selected from the group consisting of silk, sericin free silk, modified silk fibroins, polyglycolic acid (PGA), polylactic acid (PLA), polylactic-co-glycolic acid (PLGA), polyhydroxyalkanoates (PHA), polyethylene terephthalate (PET), ultra-high molecular weight polyethylene (UHMWPE), blends thereof, and copolymers thereof.

4. The tissue graft of claim 1, wherein at least one of the ECM and the plurality of fibers is modified to improve adhesion between the ECM and the fiber.

5. The tissue graft of claim 1, wherein the ECM is decellularized.

6. The tissue graft of claim 1, wherein the ECM further comprises at least one progenitor cell.

7. The tissue graft of claim 1, wherein the ECM further comprises at least one biologically active molecule selected from the group consisting of vaccine antigens, clotting factors, angiogenesis factors, regulatory proteins, transcription factors, receptors, and combinations thereof.

8. A biocompatible tissue graft consisting of: an extracellular matrix (ECM) derived from collagen; and
   more than one fiber stitched into the ECM in a concentric reinforcement pattern, each of the fibers of the more than one fiber having opposing terminal ends;
   wherein the more than one fiber is disposed radially inward of edges of the graft;
   wherein the more than one fiber comprises a plurality of interconnected stitches;
   wherein the opposing terminal ends of each of the fibers are stitched together to form a continuous stitching construction;
   wherein the more than one fiber mitigates tearing and/or improves fixation retention of the graft.

\* \* \* \* \*